United States Patent
Rajapakse et al.

(10) Patent No.: US 11,202,602 B2
(45) Date of Patent: Dec. 21, 2021

(54) PERSONALIZED ASSESSMENT OF BONE HEALTH USING IMAGING

(71) Applicants: The Trustees of the University of Pennsylvania, Philadelphia, PA (US); New York University, New York, NY (US)

(72) Inventors: Chamith Sudesh Rajapakse, Cherry Hill, NJ (US); Gregory Chang, New York, NY (US)

(73) Assignees: THE TRUSTEES OF THE UNIVERSITY OF PENNSYLVANIA, Philadelphia, PA (US); NEW YORK UNIVERSITY, New York, NY (US)

( * ) Notice: Subject to any disclaimer, the term of this patent is extended or adjusted under 35 U.S.C. 154(b) by 27 days.

(21) Appl. No.: 16/208,054

(22) Filed: Dec. 3, 2018

(65) Prior Publication Data

US 2019/0183410 A1    Jun. 20, 2019

Related U.S. Application Data

(60) Provisional application No. 62/593,626, filed on Dec. 1, 2017.

(51) Int. Cl.
  *A61B 5/00*    (2006.01)
  *A61B 5/055*   (2006.01)
  *A61B 6/00*    (2006.01)
  *G16H 10/60*   (2018.01)
  *A61B 6/03*    (2006.01)
  *G16H 30/40*   (2018.01)
  *G16H 50/30*   (2018.01)
  *A61B 5/107*   (2006.01)
  (Continued)

(52) U.S. Cl.
  CPC ............ *A61B 5/4504* (2013.01); *A61B 5/055* (2013.01); *A61B 6/032* (2013.01); *A61B 6/505* (2013.01); *G16H 10/60* (2018.01); *G16H 30/40* (2018.01); *A61B 5/1072* (2013.01); *G06T 7/0012* (2013.01); *G16H 50/20* (2018.01); *G16H 50/30* (2018.01); *G16H 50/50* (2018.01)

(58) Field of Classification Search
  CPC ....... A61B 5/4504; A61B 5/055; A61B 6/505; A61B 6/032; A61B 5/1072; G16H 10/60; G16H 30/40; G16H 50/30; G16H 50/20; G16H 50/50; G06T 7/0012
  USPC ......................................................... 382/128
  See application file for complete search history.

(56) References Cited

U.S. PATENT DOCUMENTS 10,622,102 B2 *  4/2020  Itu .......................... G16H 10/60

OTHER PUBLICATIONS

Keyak. "Improved prediction of proximal femoral fracture load using nonlinear finite element models" Med Eng Phys 2001; 23(3): 165-173.*

(Continued)

*Primary Examiner* — Juan A Torres
(74) *Attorney, Agent, or Firm* — Jenkins, Wilson, Taylor & Hunt, P.A.

(57) ABSTRACT

Methods, systems, and computer readable media for non-invasively predicting patient-specific mechanical competence at an anatomical site. In some examples, a method includes receiving images from the anatomical site of a patient; using computational analysis of the images to simulate mechanical loading at the anatomical site; and generating, based on the analysis, an indication of stiffness, strength, resilience or toughness under the mechanical loading conditions.

25 Claims, 13 Drawing Sheets

(51) Int. Cl.
G16H 50/20 (2018.01)
G16H 50/50 (2018.01)
G06T 7/00 (2017.01)

(56) References Cited

OTHER PUBLICATIONS

Niebur, High-resolution finite element models with tissue strength asymmetry accurately predict failure of trabecular bone. J Biomech 2000; 33(12):1575-1583.*
Rajapakse, "Patient-specific Hip Fracture Strength Assessment with Microstructural MR Imaging-based Finite Element Modeling. Radiology," Published online Dec. 2, 2016. doi: 10.1148/radiol.2016160874.*
Chang, "Finite element analysis applied to 3-T MR imaging of proximal femur microarchitecture: lower bone strength in patients with fragility fractures compared with control subjects". Radiology 2014; 272(2):464-474.*
Orwol, "Finite element analysis of the proximal femur and hip fracture risk in older men." J Bone Miner Res 2009; 24(3):475-483.*
Chang, "Measurement reproducibility of magnetic resonance imaging-based finite element analysis of proximal femur microarchitecture for in vivo assessment of bone strength." MAGMA, 2015. 28(4): p. 407-12.*
Zhang et al., "Potential of in vivo MRI-based nonlinear finite-element analysis for the assessment of trabecular bone post-yield properties," Med. Phys., vol. 40, No. 5, pp. 1-10 (May 2013).
Lang, "Quantitative Computed Tomography," Radiol Clin N Am, vol. 48, pp. 1-12 (2010).
Rajapakse et al., "Image-Based Estimation of Trabecular Bone Mechanical Parameters at Resolutions Achievable in Vivo," Presented at the 55th annual meeting of the Orthopaedic Research Society, Las Vegas, pp. 1-1 (2009).
Bolotin, "DXA in vivo BMD methodology: An erroneous and misleading research and clinical gauge of bone mineral status, bone fragility, and bone remodeling," Bone, vol. 41, pp. 1-17 (2007).
Kanis, "Diagnosis of osteoporosis and assessment of fracture risk," The Lancet, vol. 359, pp. 1-8 (Jun. 1, 2002).
Leibson et al., "Mortality, Disability, and Nurse Home Use for Persons with and without Hip Fracture: A Population-Based Study," JAGS, vol. 50, pp. 1-7 (2002).
Keyak, "Improved prediction of proximal femoral fracture load using nonlinear finite element models," Medical Engineering & Physics, vol. 23, pp. 1-9 (2001).
Niebur et al., "High-resolution finite element models with tissue strength asymmetry accurately predict failure of trabecular bone," Journal of Biomechanics, vol. 33, pp. 1-9 (2000).
Cooper et al., "Population-Based Study of Survival after Osteoporotic Fractures," American Journal of Epidemiology, vol. 137, No. 9, pp. 1-5 (1993).
Carter et al., "New Approaches for Interpreting Projected Bone Densitometry Data," Journal of Bone and Mineral Research, vol. 7, No. 2, pp. 1-9 (1992).
Lee et al., "Rapid 3D bioprinting from medical images: an application to bone scaffolding," Proceedings vol. 10579, Medical Imaging 2018: Imaging Informatics for Healthcare, Research, and Applications, Spie Medical Imaging, pp. 1-5 (Mar. 6, 2018).
Gadaleta et al., "Fabrication of Custom PCL Scaffold for Nasal Septal Perforation Repair," Proceedings vol. 10579, Medical Imaging 2018: Imaging Informatics for Healthcare, Research, and Applications, Spie Medical Imaging, pp. 1-4 (Mar. 6, 2018).
Rajapakse et al., "Patient-specific Hip Fracture Strength Assessment with Microstructural MR Imaging—based Finite Element Modeling," Radiology, vol. 283, No. 3, pp. 1-8 (Jun. 2017).
Fernandez et al., "Investigating the Mechanical Function of he Cervix during Pregnancy using Finite Element Models derived from High Resolution 3D MRI," Comput Methods Biomech Biomed Engin, vol. 19, No. 4, pp. 1-29 (Mar. 2016).

Han et al., "Variable Flip Angle 3D Fast Spin-Echo Sequence Combined with Outer Volume Suppression for Imaging Trabecular Bone Structure of the Proximal Femur," J Magn Reson Imaging, vol. 41, No. 5, pp. 1-23 (May 2015).
Chang et al., "Feasibility of Three-Dimensional MRI of Proximal Femur Microarchiteture at 3 Tesla Using 26 Receive Elements Without and With Parallel Imaging," Journal of Magnetic Resonance Imaging, vol. 40, pp. 1-11 (2014).
Chang et al., "Finite Element Analysis Applied to 3-T MR Imaging of Proximal Femur Microarchitecture: Lower Bone Strength in Patients with Fragility Fractures Compared with Control Subjects," Radiology, vol. 272, No. 2, pp. 1-11 (Aug. 2014).
Hotca et al., "In Vivo MR Computation of Whole Proximal Femur Mechanical Competence Using Micro-Finite Element Analysis Applied to High-Resolution 3T MRI of Proximal Femur Microarchitecture," Proc. Intl. Soc. Mag. Reson. Med., vol. 22, pp. 1-2 (2014).
Kopperdahl et al., "Assessment of Incident Spine and Hip Fractures in Women and Men using Finite Element Analysis of CT Scans," J Bone Miner Res, vol. 29, No. 3, pp. 1-25 (Mar. 2014).
Kevak et al., "Effect of finite element model loading condition on fracture risk assessment in men and women: The AGES-Reykjavik study," Bone, vol. 57, No. 1, pp. 1-29 (Nov. 2013).
Zhang et al., "Assessment of trabecular bone yield and post-yield behavior from high-resolution MRI-based nonlinear finite-element analysis at the distal radius of pre- and postmenopausal women susceptible to osteoporosis," Acad Radiol., vol. 20, No. 12, pp. 1-18 (Dec. 2013).
Magland et al., "Computationally-Optimized Bone Mechanical Modeling fromm High-Resolution Structural Images," PLoS ONE, vol. 7, No. 4, pp. 1-12 (Apr. 2012).
Crandall et al., "Treatment to Prevent Fractures in Men and Women with Low Bone Density or Osteoporosis: Update of a 2007 Report," Effective Health Care Program, Comparative Effectiveness Review, No. 53, pp. 1-438 (Mar. 2012).
Link, "Osteoporosis Imaging: State of the Art and Advanced Imaging," Radiology, vol. 263, No. 1, pp. 1-15 (Apr. 2012).
Dragomir-Daescu et al., "Robust QCT/FEA Models of Proximal Femur Stiffness and Fracture Load During a Sideways Fall on the Hip," Ann Biomed Eng., vol. 39, No. 2, pp. 1-22 (Feb. 2011).
Rajapakse et al., "Computational Biomechanics of the Distal Tibia from High-Resolution MR and Micro-CT Images," Bone, vol. 47, No. 3, pp. 1-19 (Sep. 2010).
Orwoll et al., "Finite Element Analysis of the Proximal Femur and Hip Fracture Risk in Older Men," Journal of Bone and Mineral Research, vol. 24, No. 3, pp. 1-9 (2009).
Keaveny et al., "Effects of Teriparatide and Alendronate on Vertebral Strength as Assessed by Finite Element Modeling of QCT Scans in Women with Osteoporosis," Journal of Bone and Mineral Research, vol. 22, No. 1, pp. 1-10 (2007).
Yosibash et al., "A CT-based high-order finite element analysis of the human proximal femur compared to in-vitro experiments," Elsevier Science, pp. 1-34 (Mar. 1, 2006).
Wainwright et al., "Hip Fracture in Women without Osteoporosis," The Journal of Clinical Endocrinology & Metabolism, vol. 90, No. 5, pp. 1-7 (2005).
Schuit et al., "Fracture incidence and association with bone mineral density in elderly men and women: the Rotterdam Study," Bone, vol. 34, pp. 1-9 (2004).
Bolotin et al., "Inaccuracies Inherent in Dual-Energy X-Ray Absorptiometry In Vivo Bone Mineral Density Can Seriously Mislead Diagnostic/Prognostic Interpretations of Patient-Specific Bone Fragility," Journal of Bone and Mineral Research, vol. 16, No. 5, pp. 1-7 (2001).
Van Rietbergen et al., "Assessment of cancellous bone mechanical properties from micro-FE models based on micro-CT, pQCT and MR images," Technology and Health, vol. 6, pp. 1-8 (1998).
Marshall et al., "Meta-analysis of how well measures of bone mineral density predict occurrence of osteoporotic fractures," BMJ, vol. 312, pp. 1-6 (May 18, 1996).

* cited by examiner

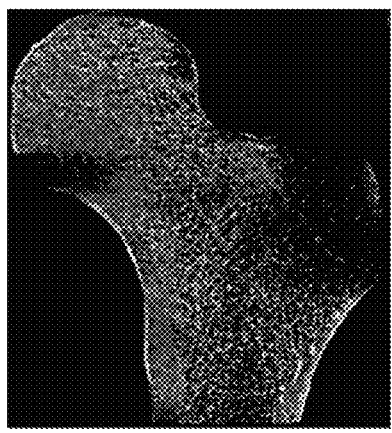
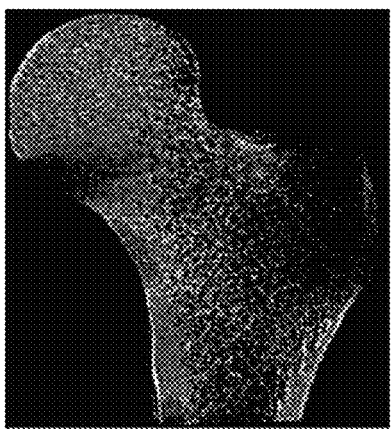
FIG. 2A         FIG. 2B         FIG. 2C
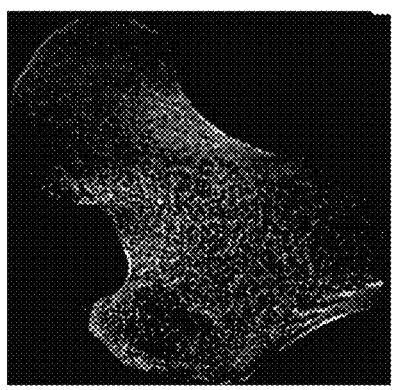
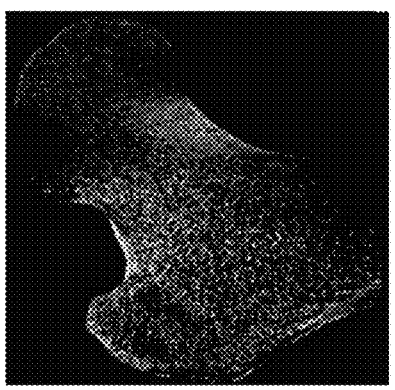
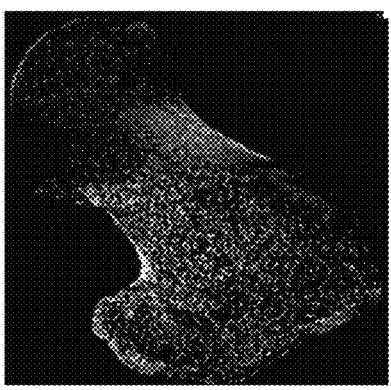
FIG. 2D         FIG. 2E         FIG. 2F

PERSONALIZED ASSESSMENT OF BONE HEALTH USING IMAGING

PRIORITY CLAIM

This application claims the benefit of U.S. Provisional Patent Application Ser. No. 62/593,626, filed Dec. 1, 2017, the disclosure of which is incorporated herein by reference in its entirety.

GOVERNMENT INTEREST

This invention was made with government support under grant numbers R01 AR 068382, R01 AR 066008, and R01 AR 070131 awarded by the National Institutes of Health. The government has certain rights in the invention.

TECHNICAL FIELD

This specification relates generally to computer analysis of medical images for non-invasively predicting patient-specific bone health.

BACKGROUND

Hip fracture is a devastating event. Within a year of injury, 20-30% of patients die and 50% lose the ability to walk. The over 300,000 hip fractures that occur in the U.S. each year account for over 40% of fracture related nursing home admissions and 70% ($12 billion) of direct costs in fracture care. In response to the clinical need for a more sensitive tool for fracture risk assessment, finite element analysis (FEA) models were developed and applied to computed tomographic (CT) images of skeletal structures to noninvasively estimate patient bone strength. However, CT-based FEA models are typically based on bone macrostructure, rather than more detailed bone microstructure. While advancements have been achieved in CT-based FEA, the section dimensions are in the order of millimeters, especially in the proximal femur, which is the site of most osteoporosis fractures. Recently, in vivo imaging of bone microstructure was achieved via magnetic resonance (MR) imaging, followed by the application of sub-regional linear FEA to MR images of bone microstructure.

Accordingly, there exists a need for methods to determine which individuals might benefit from medications that can reduce fracture risk.

SUMMARY

This specification describes methods, systems, and computer readable media for non-invasively predicting patient-specific bone health. In some examples, a method includes receiving medical images of a patient's bone; using computational analysis of the images of a skeletal region to simulate mechanical loading conditions; and generating, based on the analysis, an indication of bone health under the mechanical loading conditions.

The subject matter described herein may be implemented in hardware, software, firmware, or any combination thereof. As such, the terms "function" or "node" as used herein refer to hardware, which may also include software and/or firmware components, for implementing the feature(s) being described. In some exemplary implementations, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

FIGS. 2A-C show example strain maps of standing-fall orientations;

FIGS. 2D-F show example strain maps of sideways-fall orientations;

DETAILED DESCRIPTION

Figures 1A, 1B:
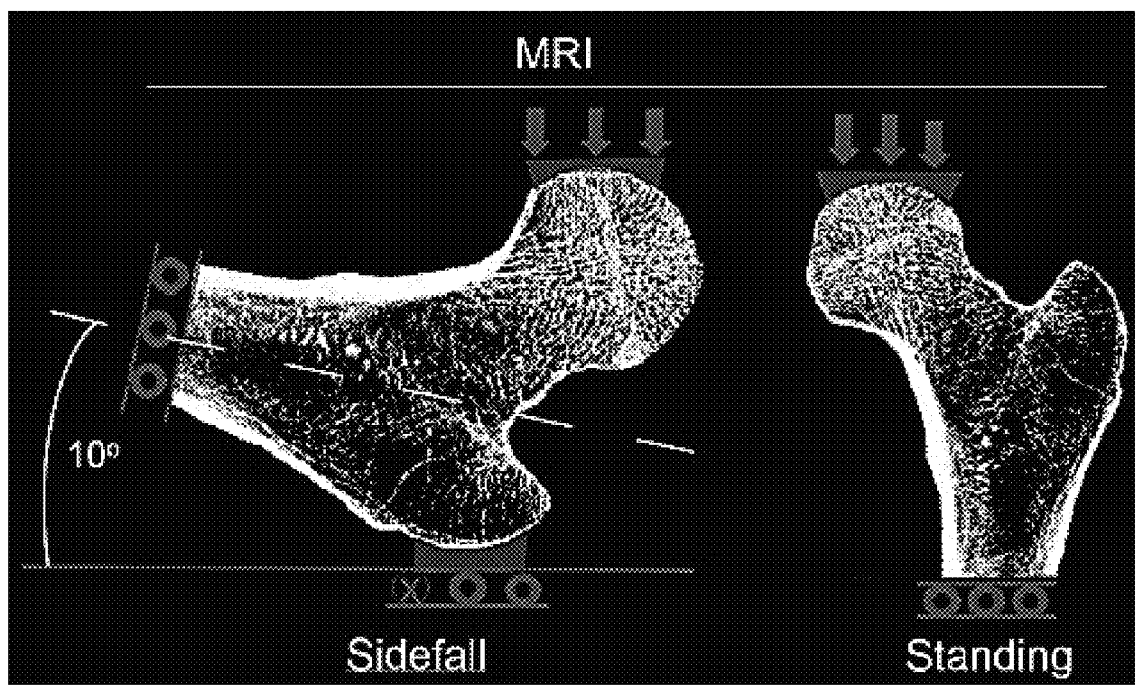
FIG. 1A is a diagram of boundary conditions for the sideways-fall and standing orientations.
FIG. 1B shows a Stress-strain curve that allows several measures of bone strength to be calculated.

The methods and systems described in this specification provide an accurate, non-invasive, reproducible and comprehensive means to assess the mechanical strength and associated fracture risk of the human bone structures such as the hip. The methodology leverages the high resolution capabilities of medical imaging, e.g., Magnetic Resonance Imaging (MRI), in order to incorporate the macro and microarchitecture of bone as a means to derive an exhaustive assessment of bone strength. By taking into account the trabeculae, which are the structural building blocks that make up the bone of the hip, we can attain an extremely detailed evaluation of the mechanical strength of the bone. The bone trabeculae can be distinguished through the acquisition of high resolution MRI images which are then analyzed through the application of Finite Element Analysis (FEA). The FEA model allows for the simulation of various loading conditions that could be experienced by the patient, for example a fall to the side. FEA takes into account the shape, geometry and distribution of the trabecular building blocks during the application of these stresses in order to provide quantitative values that comprehensively describe the bones mechanical integrity. This assessment of the bones mechanical sufficiency allows for accurate predictions of patient fracture risk.

This specification describes methods, systems, and computer readable media for non-invasively predicting patient-specific bone resilience or toughness. The methods and systems are described with respect to a study performed on the methodology.

The World Health Organization defines osteoporosis as a disease of reduced bone strength and increased fracture risk due to low bone mass and microstructural deterioration (1). Hip fractures in particular have the most devastating consequences, with a mortality rate as high as 24% in the 1st year after fracture (2,3). The standard-of-care test used to diagnose osteoporosis is dual X-ray absorptiometry (DXA) estimation of areal bone mineral density in the hip and spine (1). In vivo, lower bone mineral density correlates with higher fracture risk (1,4). However, DXA cannot demonstrate many properties of bone that contribute to bone strength (5,6). While advancements in DXA processing have greatly improved the technique by accounting for volumetric differences (7), in vivo it is susceptible to measurement error from overlying soft-tissue calcifications and not taking bone architecture into account (5,6). Most notably, DXA alone cannot be used to identify most of the individuals who are at risk for fracture. Specifically, more than 50% of those who sustain fragility fractures, including hip fractures, do not have low enough bone mineral density to meet DXA criteria for an osteoporosis diagnosis (8,9). These patients could have benefitted from existing osteoporosis medications, which are capable of reducing fracture risk by approximately 50% (10).

In response to the clinical need for a more sensitive tool for fracture risk assessment, finite element analysis (FEA) models were developed and applied to computed tomographic (CT) images of skeletal structures to noninvasively estimate patient bone strength (11-13). However, CT-based FEA models are typically based on bone macrostructure, rather than more detailed bone microstructure (14). While advancements have been achieved in CT-based FEA by using section dimensions in the order of millimeters, especially in the vertebra, our primary focus is on the proximal femur, which is the site of most osteoporosis fractures (8). Recently, in vivo imaging of bone microstructure was achieved via magnetic resonance (MR) imaging (16,17), followed by the application of sub-regional linear FEA to MR images of bone microstructure (18).

There is a need to take the next step forward in the fields of in vivo bone imaging and hip fracture risk assessment by incorporating both an individual's macro and microstructural anatomy into the assessment of mechanical competence. The purpose of our study was to describe a nonlinear FEA method by using MR images for the assessment of the mechanical competence of the hip and to demonstrate the reproducibility of the tool.

Study Design

To thoroughly assess the reproducibility of the FEA method and analysis, this study involved three separate analyses: (a) a test-retest reproducibility analysis, in which each of the first 13 subjects underwent imaging on three separate occasions to determine longitudinal variability; (b) an interoperator reproducibility analysis, where four operators independently analyzed identical image sets from the next 10 subjects and results were compared between operators for consistency; and (c) an intraoperator reproducibility analysis, where the four operators independently analyzed the same images from the same 10 participants two times, 2 weeks apart, and results were compared within operators. Additionally, a case study was performed to demonstrate the ability of the finite element method to demonstrate differences in bone strength between a patient with a fracture (MR imaging performed on the hip contralateral to the fracture) and a patient with osteoporosis but without fracture.

MR Imaging

The nondominant hip of all subjects was imaged with a 3-T whole-body MR imaging unit (Skyra; Siemens, Erlangen, Germany) by using a 26-element receive-coil setup (18 elements from a body matrix coil anteriorly and eight elements from a spine coil posteriorly). The coil was wrapped and secured around the hip. We used a three-dimensional fast low-angle shot sequence with the following parameters: repetition time (msec)/echo time (msec), 37/4.92; voxel dimensions, 0.234×0.234 mm; section thickness, 1.5 mm; 60 coronal sections; bandwidth, 200 Hz per pixel; parallel acceleration (generalized autocalibrating partially parallel acquisition) factor of two; and acquisition time, 15 minutes 18 seconds. Resolution was confirmed previously and was slightly lower than the dimensions stated in our previous work (19), and field inhomogeneity across the field of view was negligible. The 13 subjects who participated in the test-retest portion of this study each underwent imaging a total of three times (twice in one day, with repositioning between examinations, and once 1 week later). The group of 10 subjects who participated in the inter- and intraoperator section of the study and the two participants selected for a case study each underwent imaging one time on different days.

Preprocessing of Images

The periosteal border of the whole proximal femur and the acetabulum was segmented on all MR images by using freely available Firevoxel software. After segmentation of three-dimensional image data sets, the gray-scale values of the images were linearly scaled to cover the range from 0% to 100%, with pure marrow and bone intensity having minimum and maximum values, respectively (20,21). This approach allows us to account for both partial volume effects and the presence of red marrow, which may have different signal intensity than fatty marrow. We refer to the resulting three-dimensional array that represents the fractional occupancy of bone at each voxel location as the bone volume fraction map.

Development and Implementation of Nonlinear FEA Solver

Estimating femur strength from the bone volume fraction maps was performed by generating a microlevel finite element model of each femur. This technique involves the creation of a finite-element mesh, which represents each voxel in the segmented bone volume fraction map with an equally sized linear hexahedral finite element (0.234× 0.234×1.5-mm dimensions). Since there are currently no unique quantitative criteria to identify the fracture point on a simulated stress-strain curve at each finite element, we used postyield behavior of bone assumed to behave as an elastic-plastic failure theory similar to that described in the study of Betten (22). The tissue modulus of elasticity for each element was set proportionally to the gray-scale intensity range established by the bone volume fraction map (0%-100%), with 100% intensity assigned a value of 15 GPa for bone tissue (21,23). The Poisson ratio was set at 0.3 for each model. Nonlinear FEA was used, as it has been shown to enable more accurate assessment of hip strength relative to linear analysis (12). The finite element software was developed by using C++, similar to the approach described in the studies of Magland et al and Rajapakse et al (20,21).

Estimations of hip strength were performed by conducting simulations on finite element models with two different loading conditions that mimic forces sustained by the femur. The first simulation was performed in a "sideways-fall" orientation to mimic the most common direction of hip fracture injuries (FIG. 1a). This aimed to mimic displacement to the acetabular contact region of the femoral head while constraining the greater trochanter opposite the loaded surface of the femoral head. While most procedures in the literature involve the use of a generic shape to apply displacement to the femoral head, we instead segmented the bones of the pelvis and applied this shape in a patient-specific manner to more accurately demonstrate the individual differences in skeletal architecture. Other boundary conditions at the greater trochanter and shaft are similar to other established methods (24). As the displacements increase, the reaction force at the femoral head will initially increase, reach a peak point that indicates fracture (ie, MR imaging—derived strength), and finally decrease (FIG. 1b). This mechanical behavior can be simulated in a finite element model of the hip by using a tissue-level kernel defined by a hyperbolic secant with heterogeneous isotropic tissue modulus, yield strength, and post-yield properties used to describe a nonlinear stress-strain relationship at each bone voxel. Another simulation was performed to mimic loading conditions similar to "standing" orientation. Strain maps created with FEA were rendered for visualizations purposes.

FIG. 1A is a diagram of boundary conditions for the sideways-fall and standing orientations demonstrates the direction of applied force and the side restrictions. FIG. 1B shows a stress-strain (or force-displacement) curve that allows several measures of bone strength to be calculated. Bone stiffness is defined as the tangent to the initial point of the force—displacement curve (red line). The yield point is defined on the curve as the point at which plastic deformation begins to occur, obtained by using the 0.2% offset rule. Resilience is defined as the area under the curve up to the yield point. The ultimate point is defined as the point of maximum force. Toughness is defined as the area under the curve until the ultimate point.

Statistical Analysis

Intersession and interoperator variances associated with bone toughness, resilience, stiffness, ultimate load and strain, and yield load and strain were assessed, with these parameters being extracted automatically from the generated stress strain curves by using a specially designed computer script. The variance component estimates were used to compute the intraclass correlation coefficient (ICC) and the coefficient of variation (CV) as measures of reproducibility.

Results

A representative MR image, strain map, and force-displacement curve from a subject are shown in FIGS. 1A-B. There is high strain within the greater trochanter and the femoral neck, which are the most common sites of hip fracture in the setting of a sideways fall.

FIGS. 2A-C show example strain maps of standing-fall orientations. FIGS. 2D-F show examples strain maps of sideways-fall orientations. As part of the test-retest reproducibility experiment, all six strain maps are from the same individual, a 63-year-old man, and show a high degree of reproducibility over short time periods.

Figure 3A:
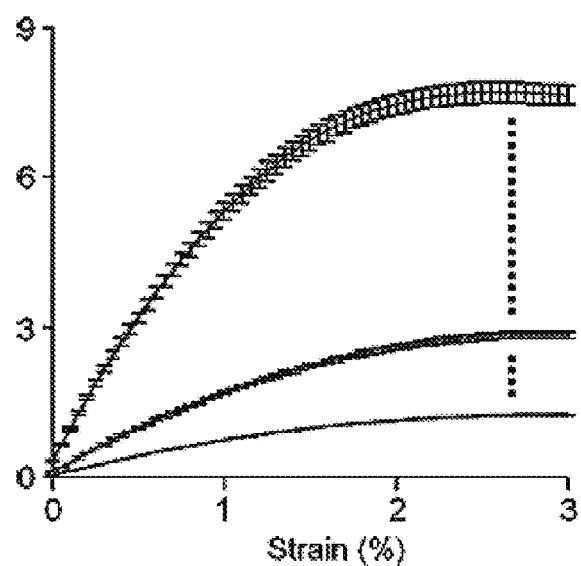
FIG. 3A is graph that shows the response of bone to applied strain in a horizontal sideways-fall position.
Figure 3B:
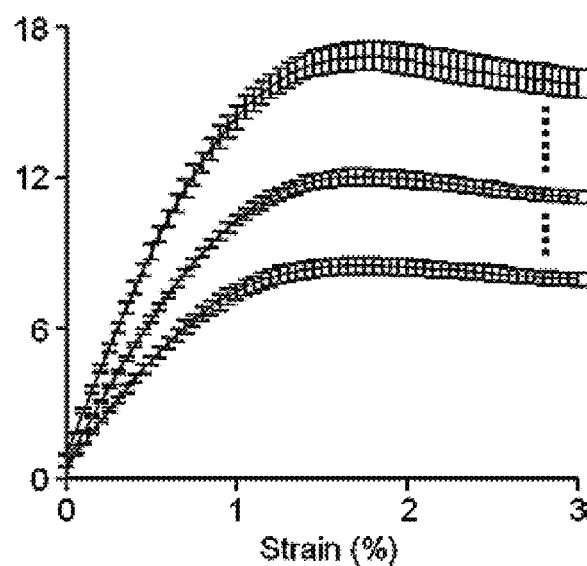
FIG. 3B is a graph that shows the response of bone to applied strain in a vertical standing position.
Figure 4A:
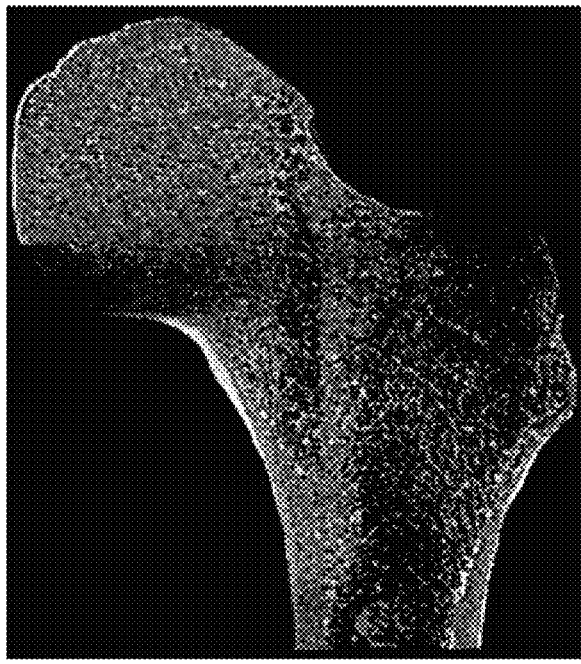
FIGS. 4A-D show a strain map comparison.
Figure 4B:
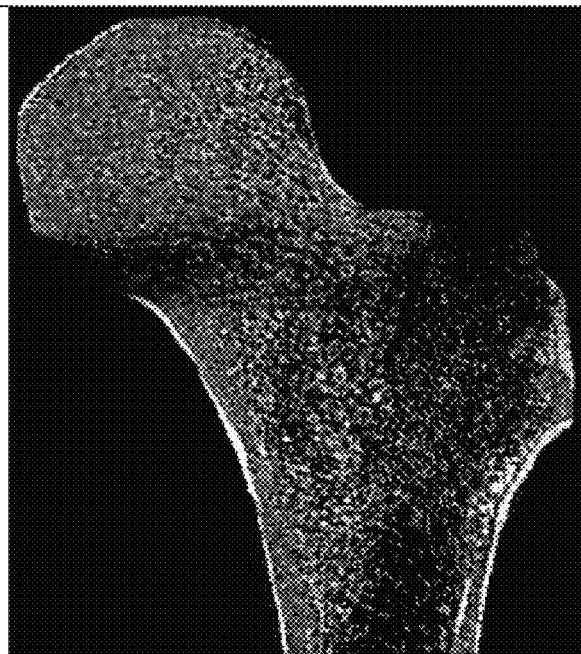
Figure 4C:
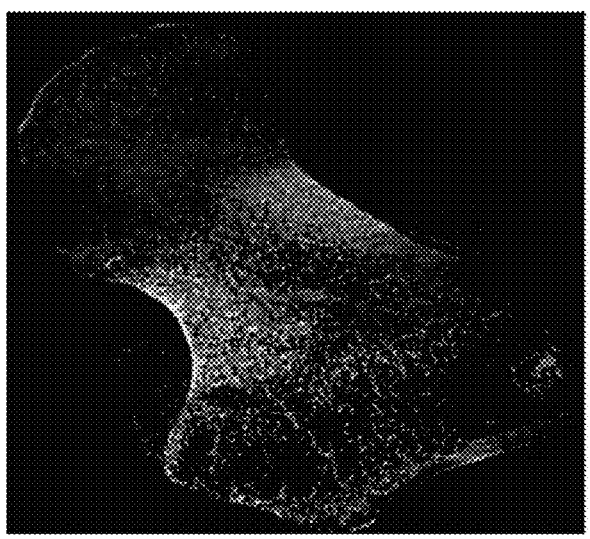
Figure 4D:
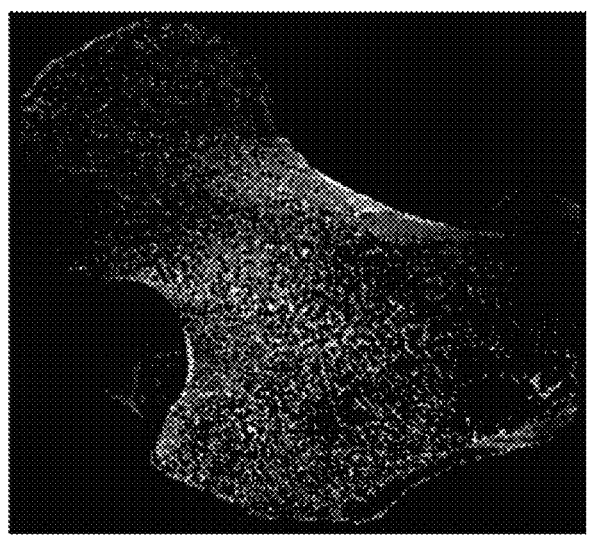

FIG. 3A is graph that shows the response of bone to applied strain in a horizontal sideways-fall position. FIG. 3B is a graph that shows the response of bone to applied strain in a vertical standing position. Each individual underwent imaging and analysis in triplicate, and the results were averaged. The strongest, weakest, and median cases from the total group of 13 individuals are displayed on each graph with standard error.

FIGS. 4A-D show a strain map comparison between (FIG. 4A, 4C) a 56-year-old woman who received a diagnosis of osteoporosis and (FIG. 4B, 4D) a "healthy" 28-year-old man with a DXA total hip T score well short of the criterion for osteoporosis (criterion of 21.2). The comparatively reduced trabecular bone volume can be seen at visual inspection in the patient with osteoporosis (FIGS. 4A and 4C); however, this patient never fractured her hip, whereas the patient on b and d sustained a hip fracture (in the contralateral femur). Regular DXA results led to classification of the patient on a and c as having a higher risk for fracture; however, the strain map clearly shows the "healthy" patient (on FIGS. 4B and 4D) to be more susceptible to fracture.

Test-Retest Reproducibility

The median CVs for proximal femur stiffness, yield strain, yield load, ultimate strain, ultimate load, resilience, and toughness for both loading configurations were all below 8% (Table 1). The ICCs for all measures were higher than 0.99, indicating a high degree of consistency and reproducibility between examinations. Individual results showed a high degree of consistency in local strains sustained by the femur within subjects between examinations (FIG. 2), while showing high variability in mechanical competence between subjects (FIG. 3).

TABLE 1

CV for the Test-Retest Study

| Parameter | Sideways-Fall Loading Configuration (%) | Standing Loading Configuration (%) |
|---|---|---|
| Stiffness | 3.16 (2.62-5.15) | 3.61 (2.82-5.33) |
| Yield strain | 0.67 (0.27-0.96) | 0.47 (0.36-0.56) |
| Yield stress | 4.07 (2.71-5.96) | 3.78 (3.20-5.14) |
| Ultimate strain | 2.55 (1.27-4.40) | 3.20 (2.35-5.27) |
| Ultimate stress | 5.38 (3.13-6.25) | 3.98 (2.96-5.42) |
| Resilience | 7.47 (6.58-9.45) | 7.96 (4.12-10.38) |
| Toughness | 5.38 (3.13-6.25) | 3.98 (2.96-5.42) |

Note.
Data are CVs, reported as medians with interquartile ranges in parentheses. Data were acquired in 13 patients who underwent three repeat imaging examinations each.

Interoperator Reproducibility

The median CVs for proximal femur stiffness, yield strain, yield load, ultimate strain, ultimate load, resilience, and toughness for both loading configurations were all below 9% (Table 2). The ICCs for all bone strength measures were higher than 0.99, indicating a high degree of consistency and reproducibility between operators. A high degree of similarity in local strains sustained by the femur was observed between images processed by different operators, while showing clear differences in mechanical competence between subjects.

TABLE 2

CV for Interoperator Reproducibility

| Parameter | Sideways-Fall Loading Configuration (%) | Standing Loading Configuration (%) |
|---|---|---|
| Stiffness | 6.17 (4.98-8.93) | 4.69 (4.15-5.13) |
| Yield strain | 0.64 (0.43-1.28) | 0.33 (0.23-0.47) |
| Yield stress | 5.96 (4.89-8.57) | 4.89 (3.99-5.18) |

TABLE 2-continued

CV for Interoperator Reproducibility

| Parameter | Sideways-Fall Loading Configuration (%) | Standing Loading Configuration (%) |
|---|---|---|
| Ultimate strain | 3.71 (3.16–6.44) | 4.55 (3.03–7.39) |
| Ultimate stress | 5.28 (4.70–8.36) | 4.52 (3.87–5.08) |
| Resilience | 6.09 (5.00–7.47) | 5.06 (4.43–5.85) |
| Toughness | 8.36 (6.37–10.42) | 8.10 (6.18–10.88) |

Note.
Data are CVs, reported as medians with interquartile ranges in parentheses. Data were acquired in 10 patients; four operators performed two repeat segmentations per patient.

Intraoperator Segmentation Reproducibility

The median CVs for proximal femur stiffness, yield strain, yield load, ultimate strain, ultimate load, resilience, and toughness for both loading configurations were all below 5% (Table 3). The ICCs for all measures were higher than 0.99, indicating a high degree of intraoperator consistency and reproducibility. Strain maps generated from the same images with repeat analysis at different times showed consistency in strain distribution across the femur.

TABLE 3

CV for Intraoperator Reproducibility

| Parameter | Sideways-Fall Loading Configuration (%) | Standing Loading Configuration (%) |
|---|---|---|
| Stiffness | 3.73 (1.82–6.24) | 3.30 (1.83–4.30) |
| Yield strain | 0.23 (0.14–0.65) | 0.20 (0.05–0.32) |
| Yield stress | 3.69 (1.82–5.80) | 3.34 (1.94–4.57) |
| Ultimate strain | 1.59 (1.07–3.66) | 1.79 (0.00–3.14) |
| Ultimate stress | 3.54 (1.76–5.55) | 3.17 (1.94–4.65) |
| Resilience | 2.90 (1.61–6.15) | 3.32 (1.79–5.90) |
| Toughness | 4.96 (2.51–8.38) | 3.62 (2.11–7.17) |

Note.
Data are CVs, reported as medians with interquartile ranges in parentheses. Data were acquired in 10 patients; four operators performed two repeat segmentations per patient.

Fracture Versus Nonfracture Identification

As a case study, one participant who received a diagnosis of osteoporosis with DXA but who did not have a history of bone fractures and another subject who sustained a hip fracture but did not meet the diagnosis criteria for osteoporosis with DXA both underwent identical MR imaging examinations and nonlinear FEA procedures on the right proximal femur. Despite being almost 3 decades older and having been classified as osteoporotic according to DXA findings, the subject without fracture showed superior mechanical competence with our approach, compared with the patient with fracture who received a diagnosis of not being osteoporotic according to DXA—with 9% greater ultimate strength in the standing configuration (12.54 kN vs 11.51 kN, respectively) and 25% greater ultimate strength in the sideways-fall configuration (10.96 kN vs 8.80 kN, respectively) (FIG. 4).

Discussion

We described the development and application of a nonlinear finite element approach to compute whole femur strength under two realistic loading conditions based on images of bone microstructure of the hip obtained in vivo. Our approach accounts for the contribution of an individual's own bone microstructure within the proximal femur on the whole femur strength. Since osteoporosis is ultimately a disease of reduced bone strength due to both low bone mass and deterioration in bone microstructure, a test that permits noninvasive estimation of bone strength and accounts for alterations in bone microstructure is highly desired. Additionally, we showed the high measurement reproducibility of the nonlinear finite element method, both for MR imaging examinations performed on the same day and on different days and for MR images segmented by the same user and by different users. The measurement reproducibility is within a range suitable for clinical cross-sectional studies of disease states or longitudinal studies of disease progression or treatment response. We also showed in a case study the potential of our approach to allow identification of patients at risk for hip fracture compared with the current clinical standard of DXA.

Our work bridges the previous technology gap that was separating the in vitro and in vivo realms of noninvasive bone strength assessment. Specifically, in the in vitro setting, nonlinear FEA has been applied to images of proximal femur microstructure obtained with micro-CT (25). In the in vivo setting, nonlinear FEA has been applied to images of proximal femur macrostructure (obtained with clinical CT) (26) or to images of distal radius and/or tibia microstructure (obtained with thin section peripheral quantitative CT or MR imaging) (13) but never to images of proximal femur microstructure. The reason why nonlinear FEA applied to images of proximal femur microstructure is important is because nonlinear models are considered more accurate than linear models, and finite element modeling based on bone microstructure is more accurate than finite element methods based only on bone macrostructure (12).

The biomechanics approach used for our study provides a unique advantage when paired with the in vivo MR images of bone microstructure that were not available previously. We have developed a model that accounts for bone microstructure in a highly detailed manner while maintaining a quick and inexpensive analysis process that does not require specialized, costly computer equipment. This would allow for the future dissemination of both the imaging process and finite element modeling code to apply as a useful clinical tool for diagnostic studies and also for longitudinal studies of bone strength and fracture prediction in larger populations. The flexible application of the model to multiple orientations provides a more comprehensive tool to determine fracture risk and guide potential interventions.

The demonstration of reliable and consistent measures of bone strength gained from this study sets the stage for future clinical cross-sectional and longitudinal studies. The reproducibility of bone strength measures between operators and across patient visits is within a range that would be suitable for continuation of the method in a larger longitudinal cohort to reliably track changes in bone structure over time and in response to interventions and treatments. Until now, there has been no practical method for finite element modeling of the whole proximal femur that takes account of bone microstructure and is also not heavily dependent on outsized levels of computing power. Our FEA model can be favorably compared with one described by Dragomir-Daescu et al, which required 1 week to perform analysis on a model with approximately 2 million elements (27); our model involved 3-4 million elements, and analysis could be completed within 30 minutes on a powerful desktop computer.

Additionally, the case study performed between the patient with fracture and the patient without fracture suggests that finite element measures may provide additional useful information about fracture risk beyond traditional DXA T scores. The subject who had not received a diagnosis of osteoporosis still sustained a hip fracture not long before the MR imaging examination. In comparison, the subject who received a diagnosis of osteoporosis according to a low DXA hip T score had not sustained any fracture. Our finite element model showed that the "healthy" patient according to DXA was still at a higher risk of fracture (in the hip that had not been fractured) than the patient who received a diagnosis of osteoporosis with DXA. This ability to provide useful additional information about bone quality and fracture risk could allow clinicians to more accurately assess fracture risk in patients than if we used DXA alone. Future research should focus on the development of a comprehensive metric of bone fracture risk that includes FEA modeling, as well as successful existing techniques (28).

Potential limitations of our study include the careful oversight by an experienced musculoskeletal radiologist and other research staff to quality check MR measurements and train the operators for image segmentation. While such attention to reproducibility likely improved the consistency of our results, future studies could also include reliable and experienced investigators to quality check images before analysis. The development of best practice guidelines to support investigators in future studies is important. Another limitation of our study is that we did not calibrate the strain values on strain maps in terms of percentage of microstrain. Strain maps are designed to be purely illustrative of how greater strain can be visually represented and how accurate quantification of the relationship between voxel intensity and absolute strain value is not possible.

In conclusion, we have described a nonlinear FEA method by using MR images for the assessment of mechanical competence of the hip and demonstrated the reproducibility of the tool. Our experiment demonstrates that the FEA model can consistently and reliably provide fracture risk information on correctly segmented bone images. Future clinical trials could include a much larger cohort of postmenopausal women to test the relevance of our technique in monitoring disease progression and treatment effectiveness.

Figure 5:
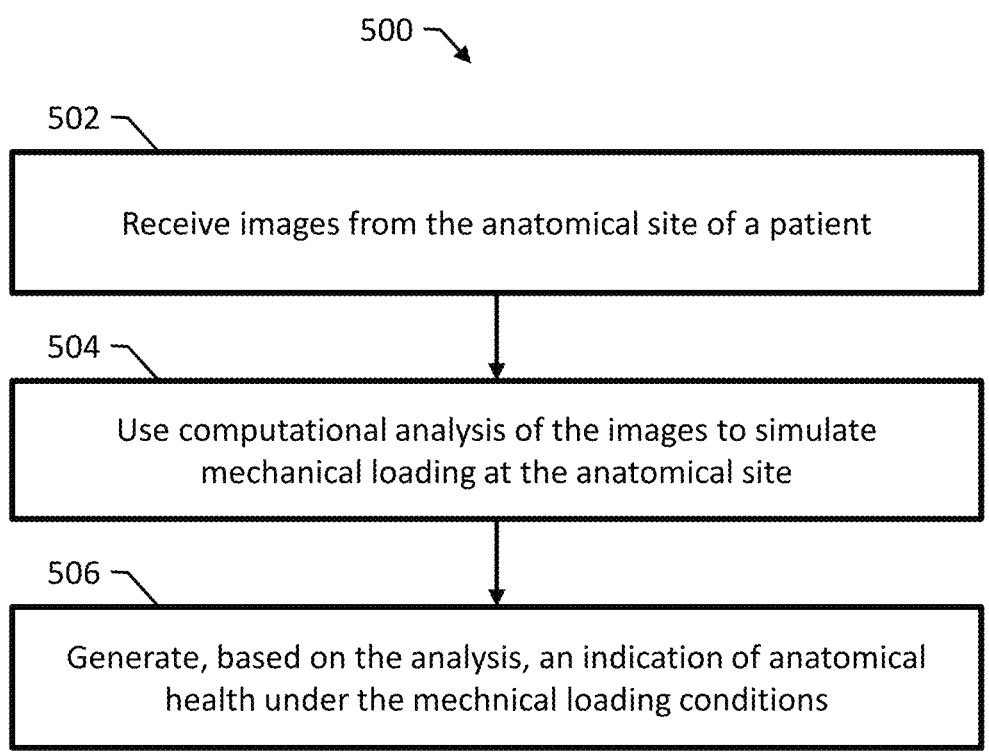
FIG. 5 is a flow diagram of an example method for non-invasively predicting patient-specific mechanical competence at an anatomical site.

FIG. 5 is a flow diagram of an example method 500 for non-invasively predicting patient-specific mechanical competence at an anatomical site. The method 500 includes receiving images from the anatomical site of a patient (502); using computational analysis (e.g., finite element analysis) of the images to simulate mechanical loading at the anatomical site (504); and generating, based on the analysis, an indication of anatomical health (e.g., mechanical competence, strength, resilience or toughness) under the mechanical loading conditions (506). Based on the indication of anatomical health, an appropriate treatment, change in existing treatment, or other intervention may be performed.

Figure 6:
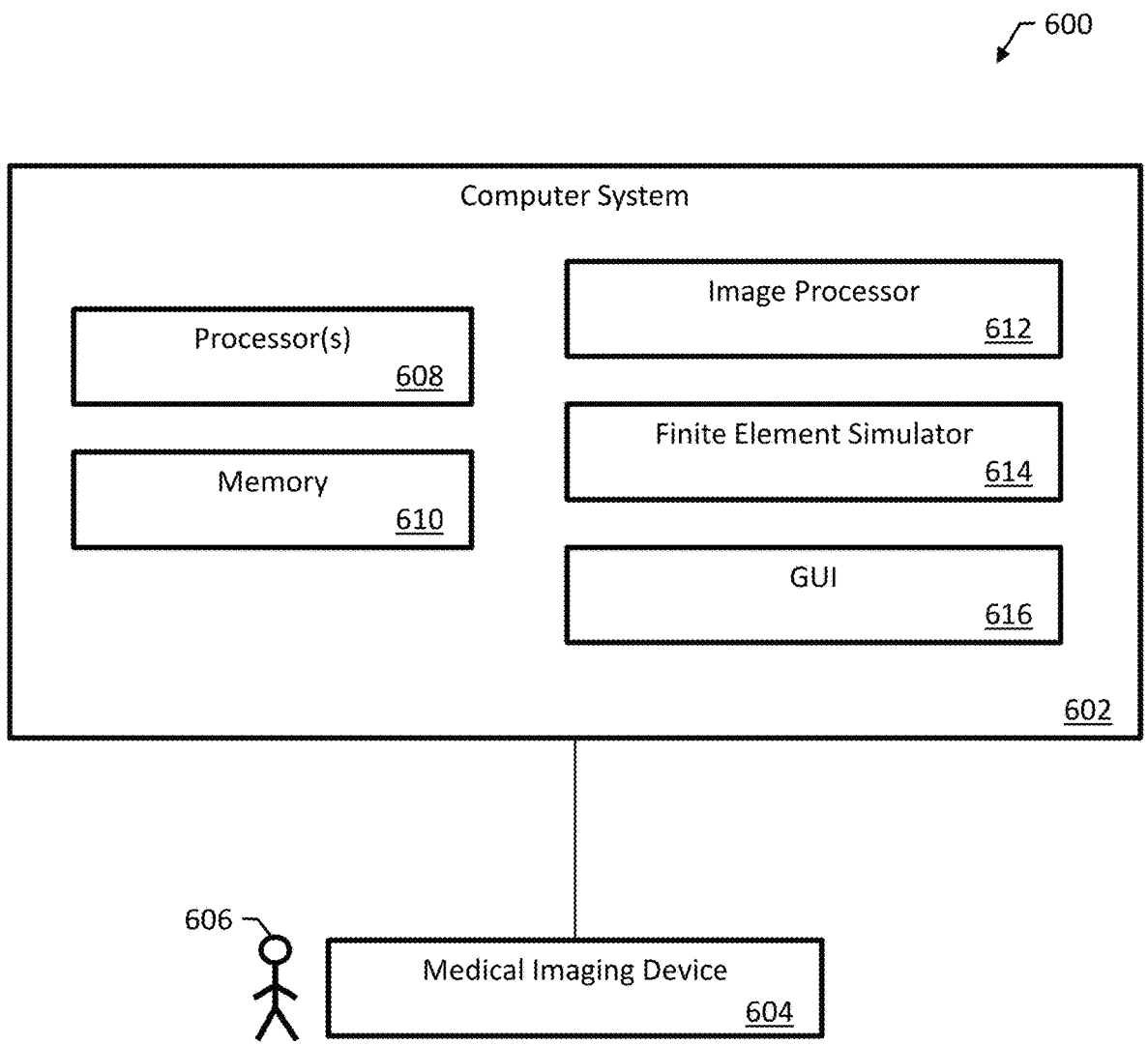
FIG. 6 is a block diagram of an example system for non-invasively predicting patient-specific mechanical competence at an anatomical site.

FIG. 6 is a block diagram of an example system 600 for non-invasively predicting patient-specific mechanical competence at an anatomical site. The system 600 includes a computer system 602 and a medical imaging device 604 configured for acquiring images of a patient 606. The medical imaging device 604 can be, e.g., an MRI device. The medical imaging device 604 acquires images of the patient 606, e.g., images of the patient's femur or other appropriate anatomical site, and provides the images to the computer system 602, e.g., over a data communications network.

The computer system includes one or more processors 608 and memory 610 storing executable instructions for the processors 608. The computer system includes an image processor 612, a finite element simulator 614, and a graphical user interface (GUI) 616. The image processor 612 is configured, by virtue of appropriate programming, for receiving images from the medical imaging device 604 and processing the images, e.g., by segmenting a portion of the images depicting the anatomy of interest.

The finite element simulator 614 is configured, by virtue of appropriate programming, for using computational analysis of the images to simulate mechanical loading at the anatomical site and generating, based on the analysis, an indication of resilience or toughness under the mechanical loading conditions. The GUI 616 is configured, by virtue of appropriate programming, for selecting images and presenting the indication of resilience or toughness generated by the finite element simulator 614, e.g., by displaying the indication or transmitting the indication over a data communications network for display on a user device.

REFERENCES

The disclosure of each of the following references is incorporated herein by reference in its entirety.
1. Kanis J A. Diagnosis of osteoporosis and assessment of fracture risk. Lancet 2002; 359 (9321):1929-1936.
2. Leibson C L, Tosteson A N, Gabriel S E, Ransom J E, Melton L J. Mortality, disability, and nursing home use for persons with and without hip fracture: a population-based study. J Am Geriatr Soc 2002; 50(10):1644-1650.
3. Cooper C, Atkinson E J, Jacobsen S J, O'Fallon W M, Melton L J 3rd. Population-based study of survival after osteoporotic fractures. Am J Epidemiol 1993; 137(9): 1001-1005.
4. Marshall D, Johnell O, Wedel H. Meta-analysis of how well measures of bone mineral density predict occurrence of osteoporotic fractures. BMJ 1996; 312(7041):1254-1259.
5. Bolotin H H. DXA in vivo BMD methodology: an erroneous and misleading research and clinical gauge of bone mineral status, bone fragility, and bone remodelling. Bone 2007; 41(1):138-154.
6. Bolotin H H, Sievänen H. Inaccuracies inherent in dual-energy x-ray absorptiometry in vivo bone mineral density can seriously mislead diagnostic/prognostic interpretations of patient-specific bone fragility. J Bone Miner Res 2001; 16(5):799-805.
7. Carter D R, Bouxsein M L, Marcus R. New approaches for interpreting projected bone densitometry data. J Bone Miner Res 1992; 7(2):137-145.
8. Wainwright S A, Marshall L M, Ensrud K E, et al. Hip fracture in women without osteoporosis. J Clin Endocrinol Metab 2005; 90(5): 2787-2793.
9. Schuit S C, van der Klift M, Weel A E, et al. Fracture incidence and association with bone mineral density in elderly men and women: the Rotterdam study. Bone 2004; 34(1): 195-202.
10. Crandall C J, Newberry S J, Diamant A, et al. Treatment to Prevent Fractures in Men and Women with Low Bone Density or Osteoporosis: Update of a 2007 Report. Rockville, Md.: Agency for Healthcare Research and Quality, 2012.
11. van Rietbergen B, Majumdar S, Pistoia W, et al. Assessment of cancellous bone mechanical properties from micro-FE models based on micro-CT, pQCT and MR images. Technol Health Care 1998; 6(5-6):413-420.
12. Keyak J H. Improved prediction of proximal femoral fracture load using nonlinear finite element models. Med Eng Phys 2001; 23(3):165-173.
13. Niebur G L, Feldstein M J, Yuen J C, Chen T J, Keaveny T M. High-resolution finite element models with tissue strength asymmetry accurately predict failure of trabecular bone. J Biomech 2000; 33(12):1575-1583.
14. Lang T F. Quantitative computed tomography. Radiol Clin North Am 2010; 48(3):589-600.

15. Keaveny T M, Donley D W, Hoffmann P F, Mitlak B H, Glass E V, San Martin J A. Effects of teriparatide and alendronate on vertebral strength as assessed by finite element modeling of QCT scans in women with osteoporosis. J Bone Miner Res 2007; 22(1):149-157.
16. Chang G, Deniz C M, Honig S, et al. Feasibility of three-dimensional MRI of proximal femur microarchitecture at 3 Tesla using 26 receive elements without and with parallel imaging. J Magn Reson Imaging 2014; 40(1): 229-238.
17. Han M, Chiba K, Banerjee S, Carballido-Gamio J, Krug R. Variable flip angle three-dimensional fast spin-echo sequence combined with outer volume suppression for imaging trabecular bone structure of the proximal femur. J Magn Reson Imaging 2015; 41(5): 1300-1310.
18. Chang G, Honig S, Brown R, et al. Finite element analysis applied to 3-T MR imaging of proximal femur microarchitecture: lower bone strength in patients with fragility fractures compared with control subjects. Radiology 2014; 272(2):464-474.
19. Rajapakse C S, Magland J, Wald M J, et al. Image-based estimation of trabecular bone mechanical parameters at resolutions achievable in vivo [abstr]. Presented at the 55th annual meeting of the Orthopaedic Research Society, Las Vegas, 2009.
20. Magland J F, Zhang N, Rajapakse C S, Wehrli F W. Computationally-optimized bone mechanical modeling from high-resolution structural images. PLoS One 2012; 7(4): e35525.
21. Rajapakse C S, Magland J F, Wald M J, et al. Computational biomechanics of the distal tibia from high-resolution MR and micro-CT images. Bone 2010; 47(3):556-563.
22. Betten J. Generalization of nonlinear material laws found in experiments to multiaxial states of stress. Eur J Mech A Solids 1989; 8(5):325-339.
23. Keyak J H, Sigurdsson S, Karlsdottir G S, et al. Effect of finite element model loading condition on fracture risk assessment in men and women: the AGES-Reykjavik study. Bone 2013; 57(1):18-29.
24. Orwoll E S, Marshall L M, Nielson C M, et al. Finite element analysis of the proximal femur and hip fracture risk in older men. J Bone Miner Res 2009; 24(3):475-483.
25. Yosibash Z, Padan R, Joskowicz L, Milgrom C. A CT-based high-order finite element analysis of the human proximal femur compared to in-vitro experiments. J Biomech Eng 2007; 129(3):297-309.
26. Kopperdahl D L, Aspelund T, Hoffmann P F, et al. Assessment of incident spine and hip fractures in women and men using finite element analysis of CT scans. J Bone Miner Res 2014; 29(3):570-580.
27. Dragomir-Daescu D, Op Den Buijs J, McEligot S, et al. Robust QCT/FEA models of proximal femur stiffness and fracture load during a sideways fall on the hip. Ann Biomed Eng 2011; 39(2):742-755.
28. Link T M. Osteoporosis imaging: state of the art and advanced imaging. Radiology 2012; 263(1):3-17.

Influence of Bone Lesion Location on Bone Strength

The system 600 of FIG. 6 can also be used to analyze the influence of bone lesion location on bone strength. The following section describes a study illustrating example systems and methods for analyzing the influence of bone lesion location on bone strength.

Currently, clinical determination of pathologic fracture risk in the hip is conducted using measures of defect size and shape in the stance loading condition. However, these measures often do not consider how changing lesion locations or how various loading conditions impact bone strength. The goal of this study was to determine the impact of defect location on bone strength parameters in both sideways fall and stance loading conditions. We recruited 20 healthy, female participants ages 48-77 for this study. We obtained in vivo high-resolution MRI of the proximal femur using a 3-T whole-body clinical MRI scanner. Using these images, we simulated 10 mm cylindrical pathologic defects in the greater trochanter, superior, middle, and inferior femoral head, superior, middle, and inferior femoral neck, and lateral, middle, and medial proximal diaphysis to determine the effects of defect location on changes in bone strength parameters by performing finite element analysis (FEA). We compared the effects of each osteolytic lesion on unaffected bone to determine changes in bone parameters in both stance and sideways fall loading conditions. We determined the predictive value of the linear parameter stiffness for these nonlinear parameters of bone strength. Stiffness may be a useful tool to predict yield stress, overall stress, and resilience. The data showed that MRI-based FEA models are useful for determining the effects of pathologic lesions on bone strength.

Introduction

A pathologic fracture has been defined as a fracture caused by the weakening of bone structure by a disease or disorder, such as cancer, which can result in increased bone fragility and fracture with minimal forces applied, such as those forces and that mechanical environment typical of daily activity [1]. Of the million new cases of cancer each year, 7-27% of patients are likely to experience a metastatic bone defect, which can increase the risk of pathologic fracture [2]. In such patients, bone strength reductions caused by pathologic fractures have severe consequences on morbidity and quality of life.

Certain bone pathologies, such as cancer, may result in lesions applied to different parts of the bone [3]. These pathologies can be particularly dangerous in the femur, where high loads are placed during activities of daily movement. The femur, particularly the proximal end, supports a significant amount of weight at the regions in contact with the hip joint [4]. Forces on the proximal femur range from 3.5 times body weight during the mid-stance phase of gait to 7.7 times body weight during stair climbing [5, 6]. Additional osteolytic lesions can severely reduce bone strength, and thus patient mobility, which can contribute to increasing patient mortality [7]. Past studies have found that high-risk, osteolytic lesions produced in cadaveric proximal femurs may decrease bone strength by up to 50% [8].

Depending on the location of the lesion, bone strength may be impacted differently based on load distribution [9]. Understanding the relationship between bone strength and lesion location may aid in the determination of femoral fracture risk [10]. Long-held guidelines to determine high-risk pathologic fractures include a defect 2.5 cm in dimension and >50% cortical destruction as indications for prophylactic stabilization. In vitro studies suggest that these clinical guidelines of a 2.5 cm defect and 50% cortical destruction are associated with large errors in estimation of the load-bearing capacity of a bone [1]. Sixty to over 90% reductions in load-bearing capacity can be observed with the commonly cited 50% cortical involvement. This large variation in strength reduction, combined with radiographic defect size measurement errors as large as 100%, are the major reasons clinical studies have failed to produce consistent and objective radiographic guidelines for predicting pathologic fracture [11].

To predict the risk of pathologic fracture, Mirels developed a scoring system based on radiographic criteria (location [upper limb, lower limb, or trochanteric region], degree of cortical involvement [<33.3%, 33.3% to 66.6%, or >66.6%], and nature of lesion [lytic, blastic, mixed]) and degree of pain (mild, moderate, functional) [12]. However, the Mirels criteria lack specificity and do not account for other properties of bone that can influence its strength [13]. While dual-energy X-ray absorptiometry (DXA) has been used for predicting osteoporotic fracture, it has not been useful in the setting of pathologic fractures [14]. DXA is not an accurate tool for investigating bone strength, as it cannot assess bone response to mechanical loading, which is crucial information for predicting risk of bone fracture. To better determine bone strength and calculate fracture risk, researchers and physicians have used quantitative computed tomography (CT) in place of DXA imaging [15]. While there is evidence that CT is more accurate than the Mirels criteria, CT exposes the patient to increased ionizing radiation while also not providing microstructural bone information [16, 17]. Focusing on bone microstructure and lesion location in the proximal femur using high-resolution magnetic resonance imaging (MRI) and finite element analysis (FEA), which does not expose patients to any ionizing radiation and produces more data about bone microstructure, rather than bone macrostructure, may provide valuable information for clinical assessment, treatment, and prevention of pathologic fracture [18].

The primary goal of this study was to investigate how the site of bone pathology influences the reduction in bone strength at the proximal femur using high-resolution MRI and FEA, which ultimately can provide a general model for longitudinal, noninvasive patient monitoring and a potential means of future individualized bone strength profiling. The secondary goal of this study was to mimic and analyze the degree of influence that varying bone pathology sites have on the bone strength of patients during conditions of normal weight-bearing and traumatic impact. The third goal of this study was to determine the predictive value of stiffness, a simple linear calculative parameter to assess bone strength, in determining more nonlinear parameters such as bone resilience, yield stress, overall stress, and toughness.

Study Population

This HIPAA compliant study was approved by the institutional review board and written informed consent was obtained from all participants. Twenty healthy, female participants were recruited (mean age=62.15±7.78 years; age range=48-77 years) from our institution with total hip dual-energy X-ray absorptiometry (DXA) results spanning from osteopenia to osteoporosis (mean total hip BMD T-score=−2.025±0.597, range=−1.2 to −2.7), approximately normal body mass indexes (BMI; mean BMI=21.72±3.23), and no history of fragility fractures.

MRI Scanning and Image Pre-Processing

For all participants, the nondominant hip was imaged with a 3-T whole-body MR imaging unit. In vivo high resolution MRI images of the hip were obtained using a 26-element receive-coil set up, with 18 elements from a body matrix coil anteriorly and eight elements from a spine coil posteriorly, and using a coil wrapped and secured around the hip [19-22]. All 20 participants were scanned using a 3-Dimensional Fast Low-Angle Shot Sequence (FLASH), with scan parameters consisting of: a repetition time (TR) of 37 ms, an echo time (TE) of 4.92 ms, 0.234 mm×0.234 mm, 60 coronal slices, a slice thickness of 1.5 mm, a bandwidth of 200 Hz/pixel, a parallel acceleration (generalized auto calibrating partially parallel acquisition) factor of 2, and an acquisition time of 15 minutes 18 seconds [20].

Freely available Firevoxel software was used to segment all 3-dimensional image data sets for the periosteal border of the whole proximal femur and the acetabulum [21]. To account for partial volume effects and distinguish between red marrow and fatty marrow, which possess varying signal intensities, grayscale values were linearly scaled from 0% for minimum values of pure marrow and bone intensity to 100% for maximum values of pure marrow and bone intensity [20]. A bone volume fraction (BVF) map was then generated, consisting of a 3-D array representing the fractional occupancy of bone at each voxel location [20, 21].

Nonlinear FEA

Femur strength was estimated by constructing a microlevel finite element model of each femur from BVF maps. Each voxel in the bone volume fraction map had an equally sized, hexahedral finite element with tissue modulus of elasticity set proportionally to greyscale intensity range. The 100% intensity was assigned a value of 15 GPa for bone tissue and Poisson's ratio was set at 0.3 [21]. The first of the two mechanical behavior simulations performed in this study mimicked the force exerted by the acetabular contact region of the femoral head and the constraint of the greater trochanter (opposite the loading surface) during a lateral, or sideways, fall. The second condition mimicked the weight-bearing conditions on the femur similar to standing, or stance. A kernel with heterogeneous isotropic tissue modulus, yield strength, and post-yield properties was used to describe a nonlinear stress-strain relationship in each voxel and 3-dimensional strain [21].

Pathology Simulation

Figure 7:
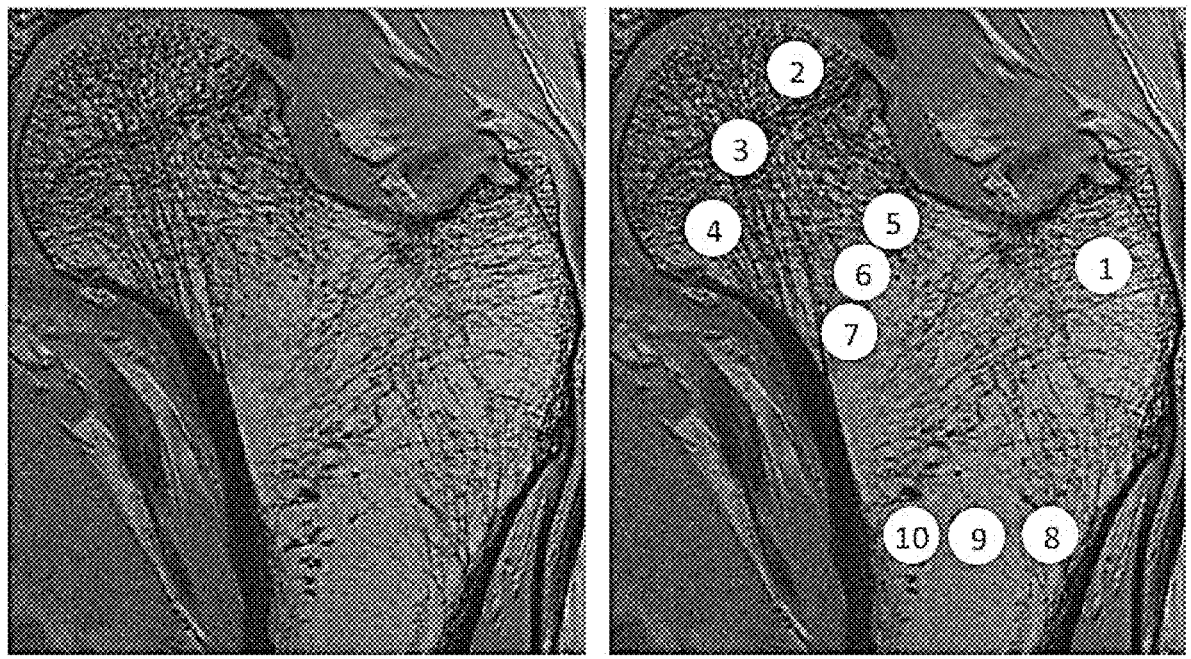
FIG. 7 shows an example image of a bone structure and simulated defect locations.

After performing these simulations as a control, a 10 mm diameter cylindrical region in the trabecular bone compartment was artificially removed from the 3D-reconstructed femur model to mimic osteolytic bone lesions. The location of artificial bone removal (lesion) varied by ten different sites: three in the femoral head (superior, middle, inferior), three in the femoral neck (superior, middle, inferior), three in the proximal diaphysis (lateral, middle, medial), and one in the greater trochanter (FIG. 7). Independent finite element analyses were then performed for each participant for stiffness, yield load, ultimate load, resilience, and toughness in standing and sideways fall loading configurations and compared to the pathology-free bone simulations. Three-dimensional strain maps provided visual representation of changes in strain distribution at a microstructure level due to simulated lesions.

Statistical Analysis

T-tests were used to determine significance and to assess the effect of the two loading conditions before and after artificial lesion creation. To assess the predictive value of the standing condition to the sideways fall condition, the significance of change in stiffness, resilience, yield stress, overall stress, and toughness before and after lesion creation was assessed between the standing condition and the sideways fall condition by using the correlation coefficient to calculate the p-value, with any p-value less than 0.05 considered significant. To assess the predictive value of the stiffness parameter for bone resilience, yield stress, overall stress, and toughness, correlations were performed between change in stiffness and the aforementioned parameters in both standing and sideways fall conditions.

Sideways Fall Loading Simulation

Figure 8:
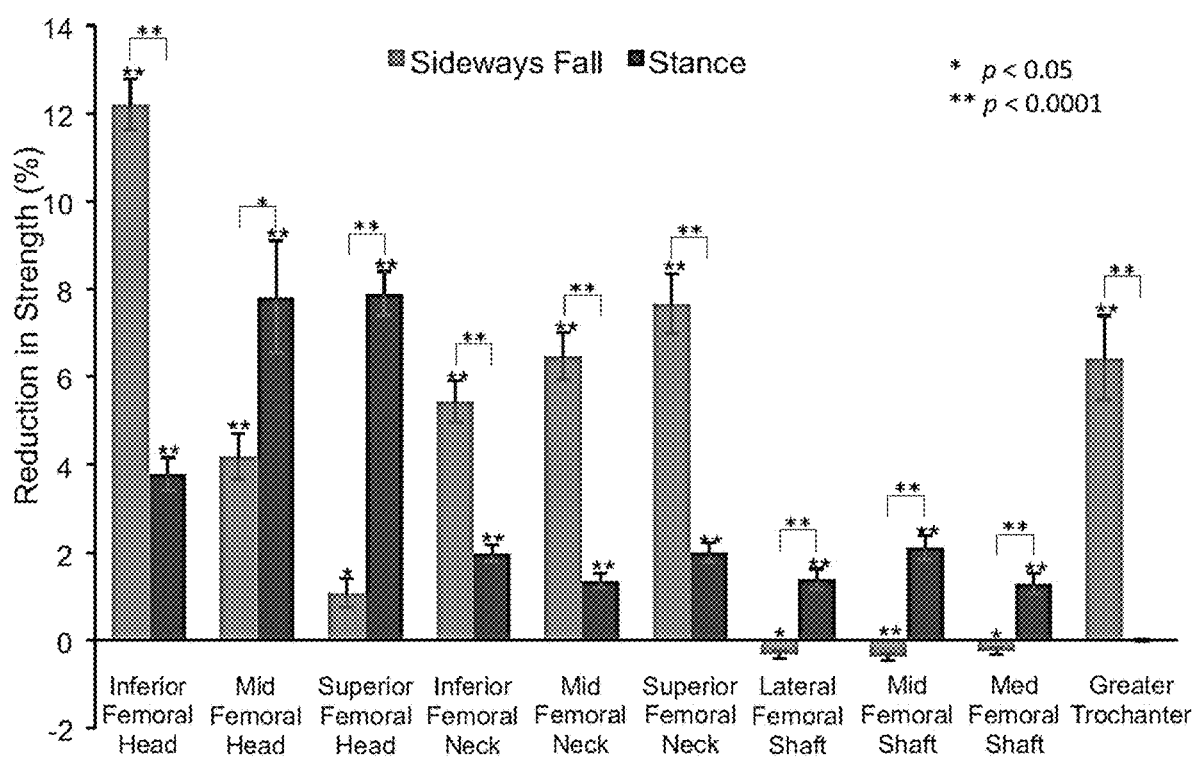
FIG. 8 is chart illustrating the reduction in strength due to defects at each location.

Under loading conditions similar to a sideways fall, a pathologic lesion in the inferior femoral head resulted in the greatest overall reduction in strength (12.21±0.58%;

p<0.0001; FIG. 8). There was a reduction of 11.28±0.73% (p<0.0001) in bone stiffness, 14.04±1.12% (p<0.0001) in yield stress, 14.93±1.56% (p<0.0001) in resilience, and 8.11±2.47% (p=0.004) when the artificial pathology was placed in the inferior femoral head. Destruction within the greater trochanter showed a similar reduction of 6.43±0.96% (p<0.0001) in overall hip strength. Additionally, there were reductions of 9.12±1.45% (p<0.0001) in stiffness, 8.53±1.08% (p<0.0001) in yield stress, and 8.61±1.26% (p<0.0001) in resilience in the hip.

Stance Loading Simulation

Figure 9:
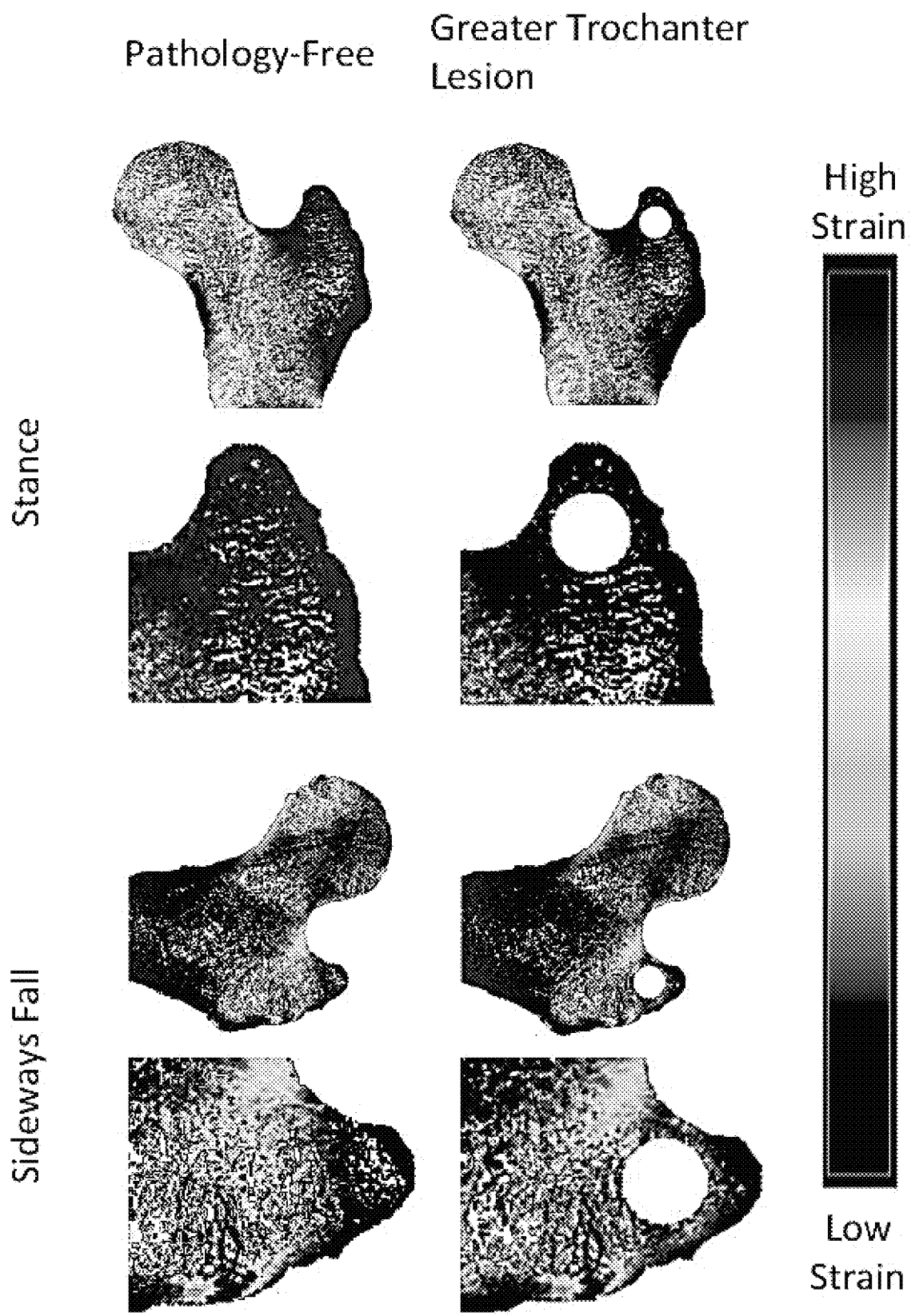
FIG. 9 illustrates strain distribution of a greater trochanter lesion.

During the simulation of weight bearing that mimics standing, the most significant decrease in overall strength occurred when the pathologic lesion was located in the mid and superior femoral head (−7.91±0.5%, p<0.0001 for a pathologic lesion located in the superior femoral head; −7.82±1.3%, p<0.0001 when located in the mid femoral head; FIG. 9). Bone stiffness decreased by 7.29±2% (p<0.0001) when the pathology was in the femoral head and neck. Yield stress decreased 8.39±1.5% (p<0.0001) with pathology located in the medial femoral head and 7.45±0.4% (p<0.0001) when in the superior femoral head. Resilience decreased by 9.22±1.4% (p<0.0001) with the destruction of the mid femoral head and by 8.21±0.9% (p<0.0001) when located in the superior femoral head. In addition, toughness decreased 13.83±3.0% (p<0.0002) with a pathologic lesion in the superior femoral head.

Changes in Internal Strain Distribution due to Simulated Defects

Figure 10:
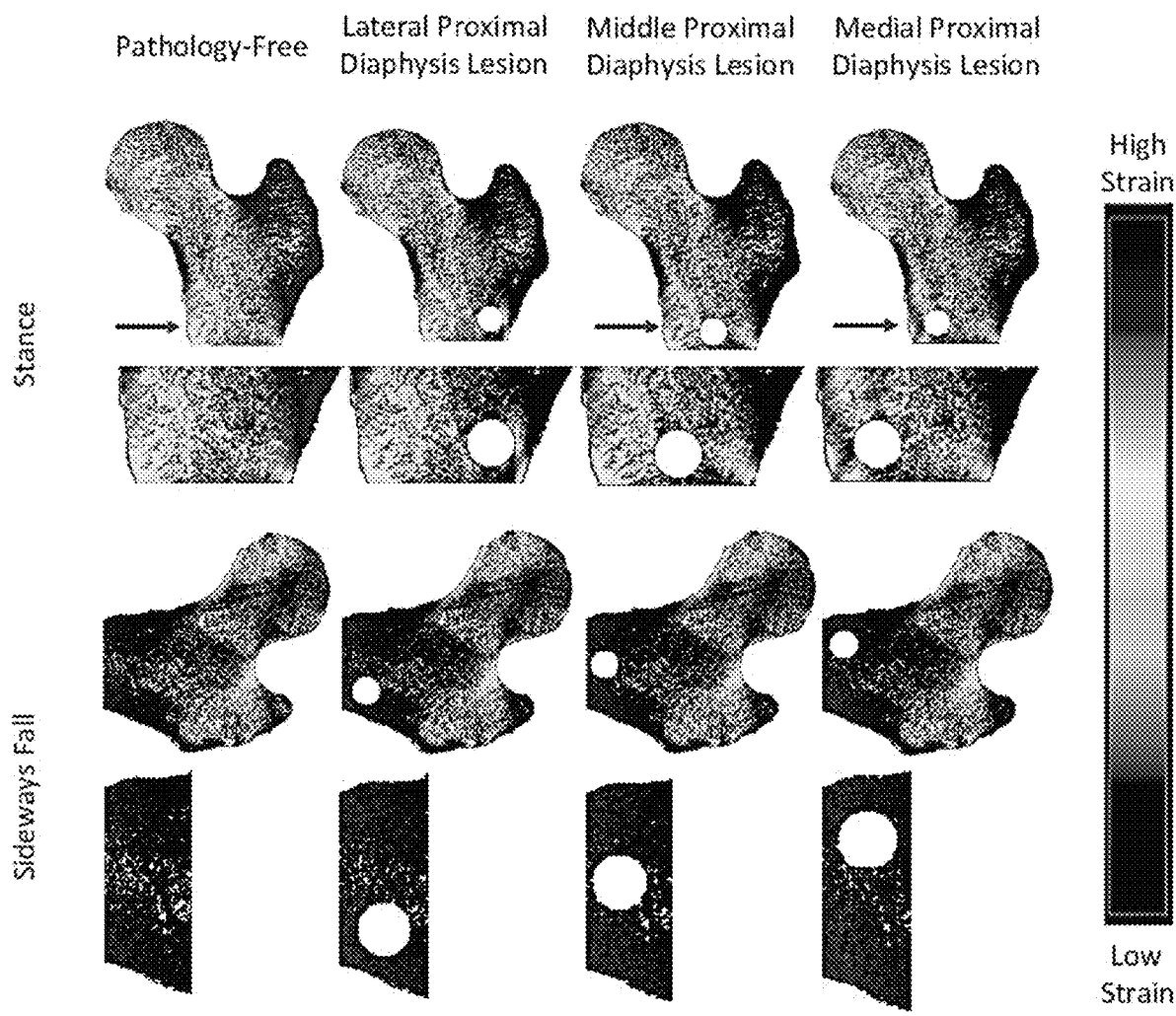
FIG. 10 illustrates strain distribution of proximal diaphysis lesions.
Figure 11:
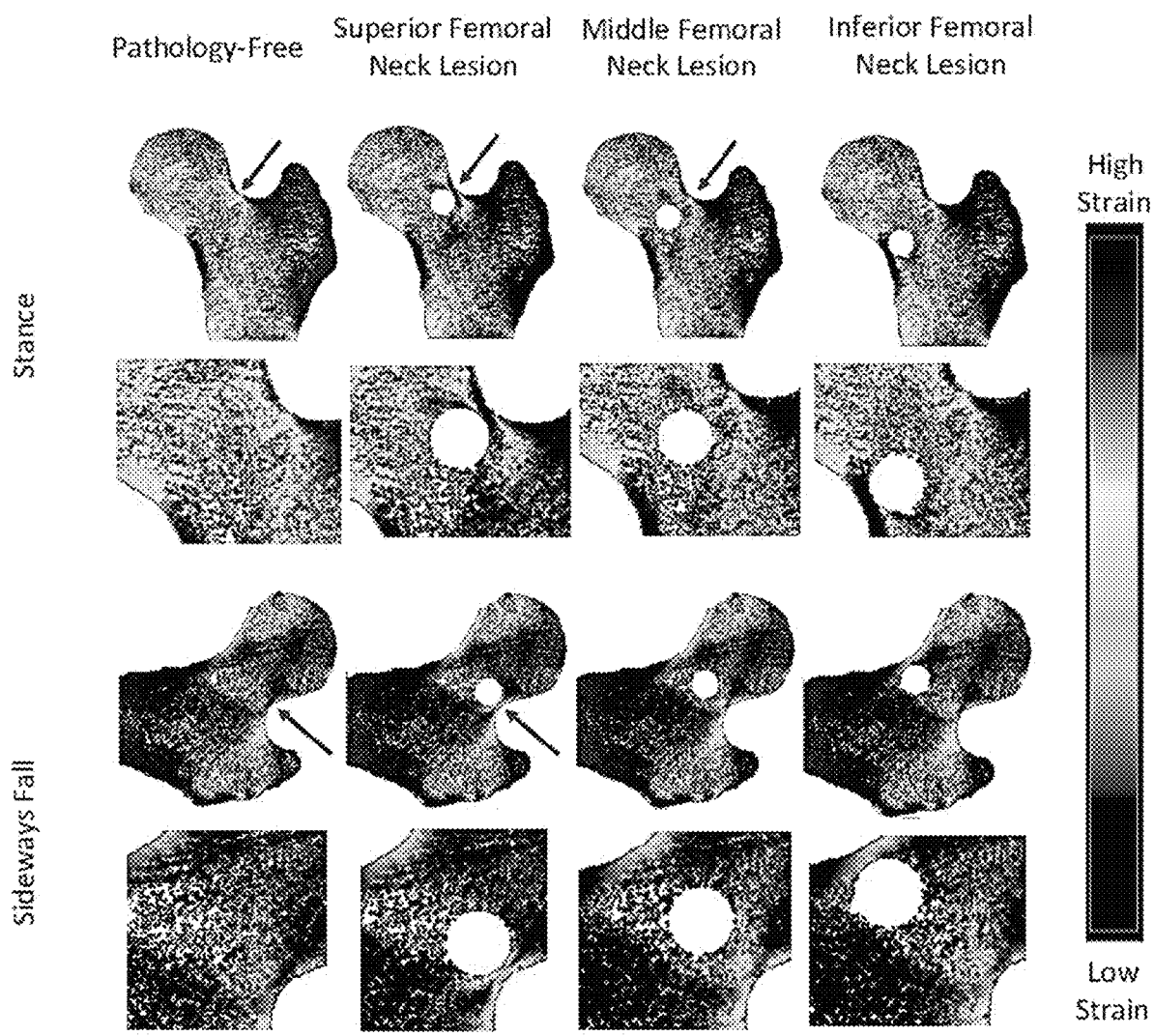
FIG. 11 illustrates strain distribution of femoral neck lesions.
Figure 12:
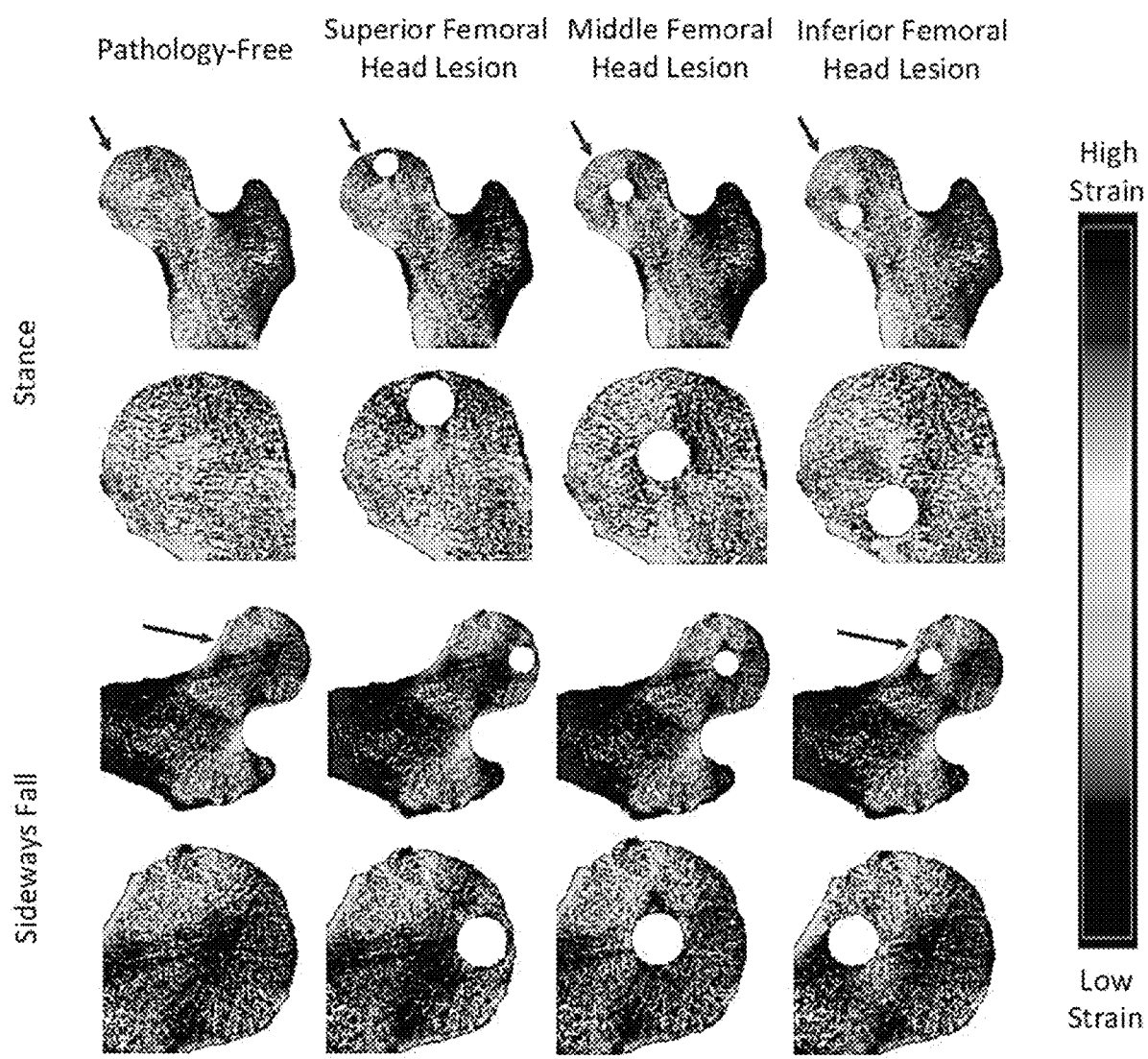
FIG. 12 illustrates strain distribution of femoral head lesions.

In the greater trochanter, there were no visible differences in the strain distribution before and after the addition of defects in the stance loading condition, but there were slight noticeable increases in strain in the sideways fall loading condition (FIG. 9). In the proximal diaphysis, however, visible increases in strain in comparison to the pathology-free simulation were noted in the mid proximal diaphysis and medial proximal diaphysis lesion simulations for the stance loading conditions, but no differences were noted in the sideways fall condition (FIG. 10). In the femoral neck, visible increases in strain in comparison to the pathology-free simulation were noted in the mid femoral neck and superior femoral neck lesion simulations for the stance loading condition, and for the superior femoral neck lesion simulation in the sideways fall loading condition (FIG. 11). In the femoral head, visible increases in strain compared to the pathology-free simulation were noted in all three of the lesion simulation stance loading conditions, and in the inferior femoral head lesion simulation in the sideways fall loading condition (FIG. 12).

Stiffness as a Predictor of Nonlinear Behavior in Stance Loading Simulation

Change in yield stress was highly positively correlated with change in stiffness in the stance loading condition for all artificial lesion locations: in the greater trochanter ($R^2$=0.82; p<0.0001), superior femoral head ($R^2$=0.91; p<0.0001), middle femoral head ($R^2$=0.99; p<0.0001), inferior femoral head ($R^2$=0.95; p<0.0001), superior femoral neck ($R^2$=0.96; p<0.0001), middle femoral neck ($R^2$=0.94; p<0.0001), inferior femoral neck ($R^2$=0.91; p<0.0001), lateral proximal diaphysis ($R^2$=0.99; p<0.0001), middle proximal diaphysis ($R^2$=0.98; p<0.0001), and medial proximal diaphysis ($R^2$=0.98; p<0.0001; Table 1). Change in overall stress was highly correlated with change in stiffness in the stance loading position for artificial lesions in the greater trochanter ($R^2$=0.84; p<0.0001), middle femoral head ($R^2$=0.93; p<0.0001), lateral proximal diaphysis ($R^2$=0.87; p<0.0001), middle proximal diaphysis ($R^2$=0.86; p<0.0001), and medial proximal diaphysis ($R^2$=0.81; p<0.0001), but had no significant trend for artificial lesions in the superior femoral head and inferior femoral head in the stance loading condition. Change in resilience was highly positively correlated with change in stiffness for artificial lesions located in the greater trochanter ($R^2$=0.97; p<0.0001), middle femoral head ($R^2$=0.80; p<0.0001), inferior femoral head ($R^2$=0.80; p<0.0001), superior femoral neck ($R^2$=1.00; p<0.0001), middle femoral neck ($R^2$=1.00; p<0.0001), lateral proximal diaphysis ($R^2$=1.00; p<0.0001), and middle proximal diaphysis ($R^2$=1.00; p<0.0001). No significant trends were found between change in resilience and change in stiffness for the superior femoral head in the stance loading condition. Likewise, no association was found between stiffness and toughness in the stance loading condition for any pathologic lesion location.

TABLE 1

Stiffness vs. parameter correlations by location in standing position.

| | Stiffness Correlations ($R^2$) Within Standing Position | | | |
| --- | --- | --- | --- | --- |
| Lesion Location | Yield Stress | Overall Stress | Resilience | Toughness |
| Greater Trochanter | 0.82**** | 0.84**** | 0.97**** | 0.11† |
| Superior Femoral Head | 0.91**** | 0.45 | 0.43 | 0.04† |
| Middle Femoral Head | 0.99**** | 0.93**** | 0.80**** | 0.11 |
| Inferior Femoral Head | 0.95**** | 0.20 | 0.80**** | 0.20 |
| Superior Femoral Neck | 0.96**** | 0.70*** | 1.00**** | 0.37 |
| Middle Femoral Neck | 0.94**** | 0.70*** | 1.00**** | 0.26 |
| Inferior Femoral Neck | 0.91**** | 0.59** | 0.63** | 0.42 |
| Lateral Proximal Diaphysis | 0.99**** | 0.87**** | 1.00**** | 0.12 |
| Middle Proximal Diaphysis | 0.98**** | 0.86**** | 1.00**** | 0.33 |
| Medial Proximal Diaphysis | 0.98**** | 0.81**** | 0.55* | 0.26 |

†Negative correlation.

Stiffness as a Predictor of Nonlinear Behavior in Sideways Fall Simulation

Change in yield stress was highly positively correlated with change in stiffness in the stance loading condition for all artificial lesion locations in the sideways fall loading condition: in the greater trochanter ($R^2$=0.96; p<0.0001), in the superior femoral head ($R^2$=0.96; p<0.0001), in the middle femoral head ($R^2$=0.87; p<0.0001), in the inferior femoral head ($R^2$=0.91; p<0.0001), in the superior femoral neck ($R^2$=0.90; p<0.0001), in the middle femoral neck ($R^2$=0.84; p<0.0001), in the inferior femoral neck ($R^2$=0.84; p<0.0001), in the lateral proximal diaphysis ($R^2$=0.87; p<0.0001), in the middle proximal diaphysis ($R^2$=0.93; p<0.0001), and in the medial proximal diaphysis ($R^2$=0.87; p<0.0001; Table 2). Change in overall stress was highly positively correlated with change in stiffness in the sideways fall loading condition for artificial lesions in the greater trochanter ($R^2$=0.84; p<0.0001), middle femoral head ($R^2$=0.88; p<0.0001), middle proximal diaphysis ($R^2$=0.80; p<0.0001), and medial proximal diaphysis ($R^2$=0.89; p<0.0001), but no significant trend was found for artificial lesions in the superior femoral head in the sideways fall loading condition. Change in resilience was highly positively correlated with change in stiffness among artificial lesions located in the lateral proximal diaphysis ($R^2$=0.99; p<0.0001), middle proximal diaphysis ($R^2$=0.98; p<0.0001), and medial proximal diaphysis ($R^2$=0.99; p<0.0001). No significant trends were found for change in resilience or change in stiffness among the superior femoral head in the sideways fall loading condition. Likewise, no significant association was found between stiffness and toughness in the sideways fall loading condition for any pathologic lesion location, except for one slight correlation observed between change in toughness and change in stiffness in the sideways fall loading condition within artificial lesions created in the middle proximal diaphysis ($R^2=0.46$; $p<0.05$).

TABLE 2

Stiffness vs. parameter correlations by location in standing position.

| Lesion Location | Stiffness Correlations ($R^2$) Within Sideways Fall Position | | | |
|---|---|---|---|---|
| | Yield Stress | Overall Stress | Resilience | Toughness |
| Greater Trochanter | 0.96**** | 0.84**** | 0.61** | 0.32 |
| Superior Femoral Head | 0.96**** | 0.20 | 0.44 | 0.21† |
| Middle Femoral Head | 0.87**** | 0.88**** | 0.46* | 0.45 |
| Inferior Femoral Head | 0.91**** | 0.52* | 0.72*** | 0.21† |
| Superior Femoral Neck | 0.90**** | 0.77*** | 0.73*** | 0.18 |
| Middle Femoral Neck | 0.84**** | 0.77*** | 0.69** | 0.27 |
| Inferior Femoral Neck | 0.84**** | 0.70*** | 0.62** | 0.21 |
| Lateral Proximal Diaphysis | 0.87**** | 0.74** | 0.99**** | 0.20 |
| Middle Proximal Diaphysis | 0.93**** | 0.80**** | 0.98**** | 0.46* |
| Medial Proximal Diaphysis | 0.87**** | 0.89**** | 0.99**** | 0.13 |

†Negative correlation.

Association between Stance and Sideways Fall Measures

Associations between stance and sideways fall parameters are summarized in Table 3. Changes in stiffness between the stance and sideways fall loading conditions were highly positively correlated among artificial lesions located in the superior femoral neck ($R^2=0.80$; $p<0.0001$), middle femoral neck ($R^2=0.92$; $p<0.0001$), and inferior femoral neck ($R^2=0.90$; $p<0.0001$). No significant trends were found between the stance and sideways fall loading conditions for changes in stiffness when artificial lesions were created in the greater trochanter, middle femoral head, lateral proximal diaphysis, middle proximal diaphysis, or medial proximal diaphysis; for changes in yield stress when artificial lesions were created in the greater trochanter, superior femoral head, middle femoral head, inferior femoral head, superior femoral neck, inferior femoral neck, lateral proximal diaphysis, middle proximal diaphysis, or medial proximal diaphysis; for changes in overall stress within the greater trochanter, superior femoral head, middle femoral head, inferior femoral head, superior femoral neck, middle femoral neck, inferior femoral neck, middle proximal diaphysis, or medial proximal diaphysis; for changes in resilience when artificial lesions were created in the greater trochanter, superior femoral head, middle femoral head, inferior femoral neck, lateral proximal diaphysis, middle proximal diaphysis, or medial proximal diaphysis; or for changes in toughness within the greater trochanter, middle femoral head, inferior femoral head, superior femoral neck, middle femoral neck, inferior femoral neck, lateral proximal diaphysis, middle proximal diaphysis, or medial proximal diaphysis.

TABLE 3

Standing position vs. sideways fall position correlations.

| Lesion Location | Standing vs. Sideways Fall Correlations ($R^2$) | | | | |
|---|---|---|---|---|---|
| | Stiffness | Yield Stress | Overall Stress | Resilience | Toughness |
| Greater Trochanter | 0.08 | 0.01 | 0.21† | 0.15† | 0.05† |
| Superior Femoral Head | 0.67** | 0.33 | 0.23 | 0.20† | 0.49* |
| Middle Femoral Head | 0.05† | 0.30 | 0.25 | 0.24† | 0.37† |
| Inferior Femoral Head | 0.57*† | 0.30† | 0.05 | 0.57*† | 0.12† |
| Superior Femoral Neck | 0.80*** | 0.47 | 0.25 | 0.64** | 0.09† |
| Middle Femoral Neck | 0.92*** | 0.45* | 0.19 | 0.66** | 0.32 |
| Inferior Femoral Neck | 0.90*** | 0.36 | 0.10 | 0.34 | 0.28 |
| Lateral Proximal Diaphysis | 0.15 | 0.44 | 0.54* | 0.13 | 0.07† |
| Middle Proximal Diaphysis | 0.23 | 0.10 | 0.40 | 0.26 | 0.03 |
| Medial Proximal Diaphysis | 0.31 | 0.33 | 0.42 | 0.07† | 0.21† |

†Negative correlation.

Discussion

High-resolution imaging of the hip depicting cortical and trabecular microstructure can be used for micromechanical modeling under two realistic loading conditions and can be performed on humans without exposing the pelvic region to ionizing radiation. While metastatic disease in bone is common in many types of cancers (e.g., renal, thyroid, breast), it is sometimes not clear if the patient would benefit from a surgical intervention compared to a non-surgical approach. The images herein provide a framework for investigating the effects of various disease processes on hipbone strength, which would allow for individualized diagnosis and treatment.

Our results demonstrate that recently developed imaging and computational tools can effectively quantify the effects of various bone pathologies on hip quality and overall strength. This approach accounts for the contribution of an individual's bone microstructure, especially in the case of osteolytic bone lesions in the proximal femur. Since osteolytic cancers create lesions in various parts of the bone, it is necessary to account for the effects of such lesions on the ability of bone to support the load of a patient under different conditions, particularly among high load-bearing regions, such as the proximal femoral head [23].

For most lesion locations, the bone strength reduction in a sideways fall is much greater than the bone strength reduction in the standing position [24]. This is because the femoral-acetabular joint is primarily made to support load under stance loading conditions [5]. During falling conditions, especially the sideways fall condition, which has the greatest impact on fracture risk [25], the femoral-acetabular joint cannot effectively serve to support patient load. When the proximal femur is weakened via same-sized osteolytic lesions in various locations, as in the case of bone pathologies such as cancer, bone strength is impacted differentially based on the normal load distribution throughout the proximal femur for each scenario. Load distribution changes during standing versus sideways fall conditions [26]. Therefore, a lesion in one location of the femoral head may impact the ability of the bone to support a sideways fall more than it may impact the ability of the bone to support standing conditions, or vice versa. Thus, when considering pathologic bone strength reduction in patients to calculate fracture risk, bone strength reduction under both loading conditions must be considered [9].

Simply relying on data regarding osteolytic lesions in the standing configuration may not accurately predict the ability of the proximal femoral microstructure to support the weight of the patient under common falling conditions. Previous studies have determined the effect of osteolytic lesion location on bone strength reduction in the femoral neck [26], but our work bridges the gap between osteolytic bone lesion strength reduction and hip fracture risk calculation by expanding this study to include the effect of osteolytic lesions throughout the proximal femur under varying loading conditions.

Our study determined the impact of simulated lesions in the greater trochanter, superior femoral head, middle femoral head, inferior femoral head, superior femoral neck, middle femoral neck, inferior femoral neck, lateral proximal diaphysis, middle proximal diaphysis, and medial proximal diaphysis in both stance and sideways fall loading conditions. The greatest decrease in strength was observed with the simulated destruction of the superior femoral head and the mid femoral head in the stance loading condition. In the sideways fall loading condition, lesions in the inferior femoral head and the greater trochanter resulted in the greatest decrease in bone strength. Bone quality properties appear to decrease during defect simulation based on load distribution during those simulated loading conditions [9]. This may suggest that, although small defects in the inferior or greater trochanter may not cause as great of a decrease in bone strength in the stance loading condition, due to their impact on bone strength in the sideways fall loading condition, they should still be of great concern to physicians upon determining fracture risk.

Additionally, our study quantified the effects of these bone pathologies on overall bone strength by examining the association between changes in linear parameters (stiffness) and nonlinear parameters (yield stress, overall stress, resilience, and toughness) from the no defect condition in both the stance loading condition and the sideways fall loading condition. Calculation of nonlinear parameters to determine bone quality in the clinical setting is intensive and computationally expensive. Using a simpler, less time-consuming linear parameter, such as stiffness, to serve as a predictor of overall bone quality may be useful to clinicians determining fracture risk and further treatment options for patients with osteolytic bone lesions in the proximal femur. In accordance with existing literature, our study found that stiffness is highly positively correlated with the nonlinear parameter yield stress and has no significant relationship with bone toughness in either the stance or sideways fall loading conditions for all simulated defect locations [27, 28]. We also found that, although stiffness is a very good predictor for overall stress and resilience in most artificial defect locations in both the stance loading and sideways fall conditions (except for defects in the inferior femoral head within the stance loading condition), it seems to be a poor predictor of these parameters when a defect is placed in the superior femoral head. This could possibly suggest that, due to the high load placed on the superior femoral head in both loading conditions, an osteolytic defect in the superior femoral head induces dramatic effects in the strength properties of the bone that cannot be explained simply by the linear parameter stiffness [9, 21].

Current clinical parameters predicting fracture risk are based on measurements taken during a stance loading condition. However, a sideways fall can greatly increase fracture risk in most patients. Our study calculated correlations between the changes in linear and nonlinear parameters in bone between the stance and sideways fall loading conditions for each simulated defect region. Strong correlations were found between the stance and sideways fall loading condition for all artificial lesions located in the femoral neck for the stiffness parameter and for artificial lesions located in the superior and middle femoral neck for resilience, suggesting that the stance loading condition may be a good predictor for few bone quality parameters in the sideways fall loading condition. Poor correlations were found for changes in all calculated bone strength parameters between stance and sideways fall loading conditions when artificial lesions were simulated in the greater trochanter, middle femoral head, middle proximal diaphysis, and medial proximal diaphysis. This suggests that when clinically determining fracture risk, the sideways fall condition must also be considered prior to determination of fracture risk for most parameters, as data from the stance loading condition alone is not a strong predictor of pathologic fracture risk in the sideways fall condition [29].

The purpose of strain mapping was to provide an easily interpretable method of viewing the internal strain distribution of a given bone under various conditions. This visual data could aid physicians in their determination of whether or not surgery is a preferable option. This analysis could also help predict the most effective method for intervention, as different conditions, such as different lesion sizes, shapes, and configurations, can be simulated and compared. This simulation is especially notable for circumstances in which a lesion causes a significantly larger increase in strain in a non-stance loading condition, such as the sideways fall, and can reveal potential dangers and limitations that would not be revealed through the traditional standing-only method.

Which osteolytic defect locations have the greatest impact on bone strength parameters is determined by the dependence on each bone region in different loading conditions. Because different bone loading conditions, such as stance and sideways fall loading conditions, have such low correlational values, they must be assessed independently to determine fracture risk. To quantity changes in bone strength, linear parameters, such as stiffness, may serve as good predictors of nonlinear parameters, such as yield stress, overall stress, and resilience, but not toughness.

Figure 13:
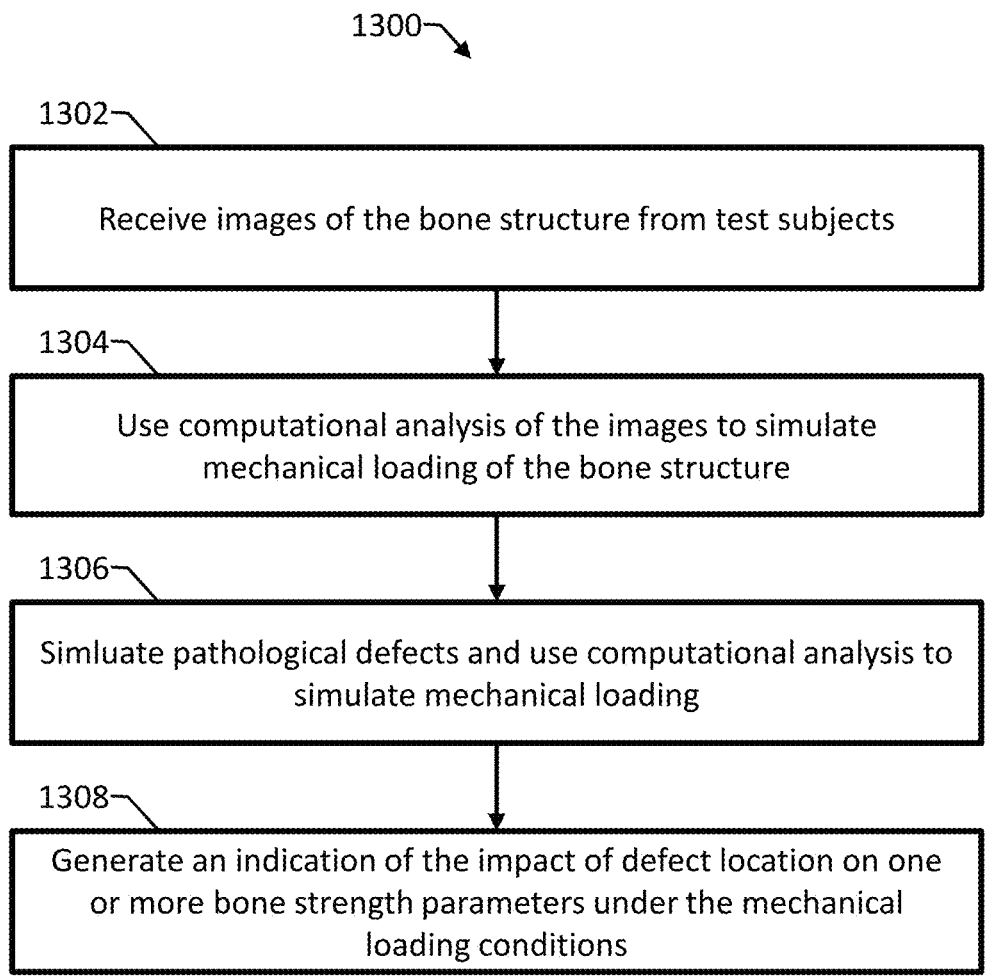
FIG. 13 is a flow diagram of an example method for analyzing bone strength.

FIG. 13 is a flow diagram of an example method 1300 for analyzing bone strength. The method 1300 includes receiving, for each subject of a number of test subjects, images of a bone structure of the subject (1302). The method 1300 includes using computational analysis of the images of the bone structure to simulate mechanical loading conditions on the bone structure (1304). The method 1300 includes simulating or analyzing, for each subject, pathological defects at a number of locations of the bone structure and using computational analysis of the images of the bone structure to simulate mechanical loading conditions on the bone structure having the pathological defects (1306). The method 1300 includes generating, based on the analysis, an indication of the impact of defect location on one or more bone strength parameters under the mechanical loading conditions (1308).

REFERENCES

The disclosure of each of the following references is incorporated herein by reference in its entirety.

1. Hipp, J. A., D. S. Springfield, and W. C. Hayes, *Predicting pathologic fracture risk in the management of metastatic bone defects.* Clin Orthop Relat Res, 1995(312): p. 120-35.

2. Hipp, J. A., et al., *Trabecular bone morphology from micro-magnetic resonance imaging.* J Bone Miner Res, 1996. 11(2): p. 286-97.

3. Toomey, A. and L. Friedman, *Mortality in cancer patients after a fall-related injury: The impact of cancer spread and type.* Injury, 2014. 45(11): p. 1710-6.

4. Crowninshield, R. D., et al., *A biomechanical investigation of the human hip.* J Biomech, 1978. 11(1-2): p. 75-85.

5. Lotz, J. C., E. J. Cheal, and W. C. Hayes, *Stress distributions within the proximal femur during gait and falls: implications for osteoporotic fracture.* Osteoporos Int, 1995. 5(4): p. 252-61.

6. Patriarco, A. G., et al., *An evaluation of the approaches of optimization models in the prediction of muscle forces during human gait.* J Biomech, 1981. 14(8): p. 513-25.

7. Zhou, Y., et al., *The effect of pathological fractures on the prognosis of patients with osteosarcoma: a meta-analysis of 14 studies.* Oncotarget, 2017. 8(42): p. 73037-73049.

8. Alexander, G. E., 3rd, et al., *Biomechanical model of a high risk impending pathologic fracture of the femur: lesion creation based on clinically implemented scoring systems.* Clin Biomech (Bristol, Avon), 2013. 28(4): p. 408-14.

9. Zani, L., et al., *Strain distribution in the proximal Human femur during in vitro simulated sideways fall.* J Biomech, 2015. 48(10): p. 2130-43.

10. Roodman, G. D., *Mechanisms of bone metastasis.* N Engl J Med, 2004. 350(16): p. 1655-64.

11. Benca, E., et al., *The insufficiencies of risk analysis of impending pathological fractures in patients with femoral metastases: A literature review.* Bone Rep, 2016. 5: p. 51-56.

12. Mirels, H., *Metastatic disease in long bones. A proposed scoring system for diagnosing impending pathologic fractures.* Clin Orthop Relat Res, 1989(249): p. 256-64.

13. Jawad, M. U. and S. P. Scully, *In brief: classifications in brief: Mirels' classification: metastatic disease in long bones and impending pathologic fracture.* Clin Orthop Relat Res, 2010. 468(10): p. 2825-7.

14. Macintyre, N. J. and A. L. Lorbergs, *Imaging-Based Methods for Non-invasive Assessment of Bone Properties Influenced by Mechanical Loading.* Physiother Can, 2012. 64(2): p. 202-15.

15. Link, T. M., *Osteoporosis imaging: state of the art and advanced imaging.* Radiology, 2012. 263(1): p. 3-17.

16. Oei, L., et al., *Quantitative imaging methods in osteoporosis.* Quant Imaging Med Surg, 2016. 6(6): p. 680-698.

17. Damron, T. A., et al., *CT-based Structural Rigidity Analysis Is More Accurate Than Mirels Scoring for Fracture Prediction in Metastatic Femoral Lesions.* Clin Orthop Relat Res, 2016. 474(3): p. 643-51.

18. de Bakker, C. M. J., et al., *Clinical Evaluation of Bone Strength and Fracture Risk.* Curr Osteoporos Rep, 2017. 15(1): p. 32-42.

19. Chang, G., et al., *Finite Element Analysis Applied to 3-T MR Imaging of Proximal Femur Microarchitecture: Lower Bone Strength in Patients with Fragility Fractures Compared with Control Subjects.* Radiology, 2014. 272(2): p. 464-74.

20. Chang, G., et al., *Measurement reproducibility of magnetic resonance imaging-based finite element analysis of proximal femur microarchitecture for in vivo assessment of bone strength.* MAGMA, 2015. 28(4): p. 407-12.

21. Rajapakse, C. S., et al., *Patient-specific Hip Fracture Strength Assessment with Microstructural MR Imaging-based Finite Element Modeling.* Radiology, 2017. 283(3): p. 854-861.

22. Chang, G., et al., *Feasibility of three-dimensional MRI of proximal femur microarchitecture at 3 tesla using 26 receive elements without and with parallel imaging.* J Magn Reson Imaging, 2014. 40(1): p. 229-38.

23. Gnudi, S., E. Sitta, and E. Pignotti, *Prediction of incident hip fracture by femoral neck bone mineral density and neck-shaft angle: a 5-year longitudinal study in postmenopausal females.* Br J Radiol, 2012. 85(1016): p. e467-73.

24. Robinovitch, S. N., W. C. Hayes, and T. A. McMahon, *Prediction of femoral impact forces in falls on the hip.* J Biomech Eng, 1991. 113(4): p. 366-74.

25. Tanck, E., et al., *Pathological fracture prediction in patients with metastatic lesions can be improved with quantitative computed tomography based computer models.* Bone, 2009. 45(4): p. 777-83.

26. Kaneko, T. S., H. B. Skinner, and J. H. Keyak, *Lytic lesions in the femoral neck: Importance of location and evaluation of a novel minimally invasive repair technique.* J Orthop Res, 2008. 26(8): p. 1127-32.

27. Zhang, N., et al., *Potential of in vivo MRI-based nonlinear finite-element analysis for the assessment of trabecular bone post-yield properties.* Med Phys, 2013. 40(5): p. 052303.

28. Miura, M., et al., *Prediction of fracture load and stiffness of the proximal femur by CT-based specimen specific finite element analysis: cadaveric validation study.* BMC Musculoskelet Disord, 2017. 18(1): p. 536.

29. Sarvi, M. N. and Y. Luo, *Sideways fall-induced impact force and its effect on hip fracture risk: a review.* Osteoporosis International, 2017. 28(10): p. 2759-2780.

30. Majumder, S., A. Roychowdhury, and S. Pal, *Simulation of hip fracture in sideways fall using a 3D finite element model of pelvis-femur-soft tissue complex with simplified representation of whole body.* Medical Engineering & Physics, 2007. 29(10): p. 1167-1178.

Although specific examples and features have been described above, these examples and features are not intended to limit the scope of the present disclosure, even where only a single example is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed in this specification (either explicitly or implicitly), or any generalization of features disclosed, whether or not such features or generalizations mitigate any or all of the problems described in this specification. Accordingly, new claims may be formulated during prosecution of this application (or an application claiming priority to this application) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A method for non-invasively predicting patient-specific mechanical competence at an anatomical site, the method comprising:

receiving images from the anatomical site of a patient;
using computational analysis of the images to simulate mechanical loading at the anatomical site, wherein the images are in-vivo images taken of a live patient, and wherein the images depict bone microstructure, and wherein using computational analysis comprises analyzing the bone microstructure depicted in the images to simulate mechanical loading at the anatomical site, and wherein analyzing the bone microstructure depicted in the images to simulate mechanical loading at the anatomical site includes simulating loading conditions in multiple directions with respect to an axis of the bone microstructure;

wherein analyzing the bone microstructure depicted in the images to simulate mechanical loading at the anatomical site includes applying loading conditions to mimic displacement to a contact region and applying a patient-specific shape to the contact region based on segmenting the anatomical site; and generating, based on the analysis, an indication of stiffness, strength, resilience or toughness under the mechanical loading conditions.

2. The method of claim 1, wherein receiving the images of the anatomical site comprises segmenting, from the images, a portion of the images depicting the anatomy of interest.

3. The method of claim 2, wherein using computational analysis of the images to simulate mechanical loading conditions comprises scaling intensity values of the images to cover a range from 0% to 100%, resulting in a volume fraction map comprising a structure that represents the fractional occupancy of tissue at each voxel of a plurality of voxels depicting the anatomical site.

4. The method of claim 3, wherein using computational analysis of the images to simulate mechanical loading conditions on the anatomical site comprises, for each voxel, setting a tissue modulus of elasticity proportionally to a scaled intensity range in a corresponding element of the volume fraction map.

5. The method of claim 4, wherein using computational analysis of the images of the anatomical site to simulate mechanical loading conditions on the anatomical site comprises simulating the mechanical loading conditions in a finite element model using a tissue-level kernel.

6. The method of claim 5, wherein the tissue-level kernel is defined by a function with pre-yield and post-yield properties used to describe a stress-strain relationship at each voxel of a plurality of voxels depicting the anatomical site.

7. The method of claim 6, wherein the anatomical site comprises a structure of a femur, and wherein using computational analysis of the images comprises simulating a stance loading condition.

8. The method of claim 6, wherein the anatomical site comprises a structure of a femur, and wherein using computational analysis of the images comprises simulating a fall loading condition.

9. A system for non-invasively predicting patient-specific mechanical competence, the system comprising:

at least one processor; and a finite element simulator implemented on the at least one processor and configured to perform operations comprising:

receiving images of an anatomical site in a patient;

using finite element analysis of the images to simulate mechanical loading conditions at the anatomical site, wherein the images are in-vivo images taken of a live patient, and wherein the images depict bone microstructure, and wherein using finite element analysis comprises analyzing the bone microstructure depicted in the images to simulate mechanical loading at the anatomical site, and wherein analyzing the bone microstructure depicted in the images to simulate mechanical loading at the anatomical site includes simulating loading conditions in multiple directions with respect to an axis of the bone microstructure;

wherein analyzing the bone microstructure depicted in the images to simulate mechanical loading at the anatomical site includes applying loading conditions to mimic displacement to a contact region and applying a patient-specific shape to the contact region based on segmenting the anatomical site; and generating, based on the analysis, an indication of the resilience or toughness of the anatomical site under the mechanical loading conditions.

10. The system of claim 9, wherein receiving the images comprises segmenting, from the images, a portion of the images depicting the anatomical site.

11. The system of claim 9, wherein using finite element analysis of the images comprises simulating the mechanical loading conditions in a finite element model using a tissue-level kernel.

12. The system of claim 9, wherein the anatomical site comprises a structure of a femur, and wherein using finite element analysis of the images comprises simulating a stance loading condition.

13. The system of claim 9, wherein the anatomical site comprises a structure of a femur, and wherein using finite element analysis of the images comprises simulating a fall loading condition.

14. The system of claim 10, wherein using finite element analysis of the images comprises scaling intensity values of the images to cover a range from 0% to 100%, resulting in a volume fraction map comprising a structure that represents the fractional occupancy of tissue at each voxel of a plurality of voxels depicting the anatomical site.

15. The system of claim 11, wherein the tissue-level kernel is defined by a function with pre-yield and post-yield properties used to describe a stress-strain relationship at each voxel of a plurality of voxels depicting the anatomical site.

16. The system of claim 14, wherein using finite element analysis of the images comprises, for each voxel, setting a tissue modulus of elasticity proportionally to a scaled intensity range in a corresponding element of the volume fraction map.

17. A non-transitory computer readable medium storing executable instructions that when executed by at least one processor of a computer control the computer to perform operations comprising:

receiving images of an anatomical site in a patient;

using finite element analysis of the images to simulate mechanical loading conditions on the anatomical site, wherein the images are in-vivo images taken of a live patient, and wherein the images depict bone microstructure, and wherein using finite element analysis comprises analyzing the bone microstructure depicted in the images to simulate mechanical loading at the anatomical site, and wherein analyzing the bone microstructure depicted in the images to simulate mechanical loading at the anatomical site includes simulating loading conditions in multiple directions with respect to an axis of the bone microstructure;

wherein analyzing the bone microstructure depicted in the images to simulate mechanical loading at the anatomical site includes applying loading conditions to mimic displacement to a contact region and applying a patient-specific shape to the contact region based on segmenting the anatomical site; and generating, based on the analysis, an indication of stiffness, strength, resilience or toughness of the anatomical site under the mechanical loading conditions.

18. A method for non-invasively predicting patient-specific anatomical properties, the method comprising:

receiving magnetic resonance images of a bone structure in a patient;

using finite element analysis of the images of the bone structure to simulate mechanical loading conditions on the bone structure, wherein the images are in-vivo images taken of a live patient, and wherein the images depict bone microstructure, and wherein using finite element analysis comprises analyzing the bone microstructure depicted in the images to simulate mechanical loading at the anatomical site, and wherein analyzing the bone microstructure depicted in the images to simulate mechanical loading at the anatomical site includes simulating loading conditions in multiple directions with respect to an axis of the bone microstructure;

wherein analyzing the bone microstructure depicted in the images to simulate mechanical loading at the anatomical site includes applying loading conditions to mimic displacement to a contact region and applying a patient-specific shape to the contact region based on segmenting the anatomical site; and generating, based on the analysis, a fracture risk assessment of the bone structure under the mechanical loading conditions.

19. The method of claim 18, wherein generating the fracture risk assessment comprises generating an indication of resilience, toughness, stiffness, or strength of the bone structure under the mechanical loading conditions.

20. The method of claim 18, wherein the bone structure comprises a bone structure of a femur, and wherein using finite element analysis of the images of the bone structure to simulate mechanical loading conditions on the bone structure comprises simulating a stance loading condition and simulating a fall loading condition.

21. A method comprising:

receiving, for each subject of a plurality of test subjects, images of a bone structure of the subject;

using computational analysis of the images of the bone structure to simulate mechanical loading conditions on the bone structure, wherein the images are in-vivo images taken of a live patient, and wherein the images depict bone microstructure, and wherein using computational analysis comprises analyzing the bone microstructure depicted in the images to simulate mechanical loading at the anatomical site, and wherein analyzing the bone microstructure depicted in the images to simulate mechanical loading at the anatomical site includes simulating loading conditions in multiple directions with respect to an axis of the bone microstructure;

wherein analyzing the bone microstructure depicted in the images to simulate mechanical loading at the anatomical site includes applying loading conditions to mimic displacement to a contact region and applying a patient-specific shape to the contact region based on segmenting the anatomical site;

simulating or analyzing, for each subject, pathological defects at a plurality of locations of the bone structure and using computational analysis of the images of the bone structure to simulate mechanical loading conditions on the bone structure having the pathological defects; and generating, based on the analysis, an indication of the impact of defect location on one or more bone strength parameters under the mechanical loading conditions.

22. The method of claim 21, wherein the bone structure comprises a structure of a femur, and wherein simulating mechanical loading conditions comprises simulating a stance loading condition.

23. The method of claim 21, wherein the bone structure comprises a structure of a femur, and wherein simulating mechanical loading conditions comprises simulating a fall loading condition.

24. The method of claim 21, wherein receiving images of the bone structure comprises receiving magnetic resonance images of the bone structure, and wherein using computational analysis comprises using finite element analysis.

25. The method of claim 21, comprising receiving images of the bone structure from a patient, determining a measure of stiffness of the bone structure using the images, and determining, based on the analysis, one or more bone strength parameters for the bone structure in the patient using the stiffness of the bone structure.

* * * * *